(12) United States Patent
Schnorr et al.

(10) Patent No.: US 8,563,268 B2
(45) Date of Patent: Oct. 22, 2013

(54) POLYPEPTIDE HAVING TYROSINASE ACTIVITY

(75) Inventors: Kirk Matthew Schnorr, Holte (DK); Jeppe Wegener Tams, Gentofte (DK)

(73) Assignee: Novozymes A/S, Bagsvaerd (DK)

( * ) Notice: Subject to any disclaimer, the term of this patent is extended or adjusted under 35 U.S.C. 154(b) by 0 days.

(21) Appl. No.: 13/203,847

(22) PCT Filed: Mar. 16, 2010

(86) PCT No.: PCT/EP2010/053393
§ 371 (c)(1),
(2), (4) Date: Aug. 30, 2011

(87) PCT Pub. No.: WO2010/106068
PCT Pub. Date: Sep. 23, 2010

(65) Prior Publication Data
US 2011/0311693 A1     Dec. 22, 2011

Related U.S. Application Data

(60) Provisional application No. 61/161,087, filed on Mar. 18, 2009.

(30) Foreign Application Priority Data

Mar. 17, 2009   (EP) ..................... 09155427

(51) Int. Cl.
*C12P 21/06*   (2006.01)
*C12N 9/02*    (2006.01)

(52) U.S. Cl.
USPC .......................................... 435/68.1; 435/189

(58) Field of Classification Search
None
See application file for complete search history.

(56) References Cited

FOREIGN PATENT DOCUMENTS

WO    WO/2006/084953  A1    8/2006

OTHER PUBLICATIONS

GenBank Accession No. U66808, Sep. 1996, 2 pages.*
Fagan et al., Mycopathologica 87:67-70, 1984.*
Birren et al, UniProt—Access No. A6SQE, 2 pages (2007).
Birren et al, UniProt—Access No. A7F6Y4, 2 pages (2007).
Birren et al, UniProt—Access No. A7FA30, 2 pages (2007).
Kruus et al Geneseq—Access No. AEJ90975, 2 pages, (2006).
Decker et al., Trends Biochemistry, vol. 25, No. 8, pp. 392-397 (2000).

* cited by examiner

*Primary Examiner* — David J Steadman
(74) *Attorney, Agent, or Firm* — Kristin J. McNamara

(57) ABSTRACT

The present invention relates to isolated polypeptides having tyrosinase activity and isolated polynucleotides encoding the polypeptides. The invention also relates to nucleic acid constructs, vectors, and host cells comprising the polynucleotides as well as methods of producing and using the polypeptides.

14 Claims, No Drawings

SEQUENCE LISTING

<160> NUMBER OF SEQ ID NOS: 16

<210> SEQ ID NO 1
<211> LENGTH: 2058
<212> TYPE: DNA
<213> ORGANISM: Trichophaea saccata

<400> SEQUENCE: 1

```
atgaagtttt cagcctttgt ggccgtggcc accacctcgg tcgtcgcact gctttccggc      60
agtgttgaag cgcaacaacc cgttccaaac ttctaccccg tccgtggagc cattgcctgg     120
accaactccg ttgtgcggcg tttgccgctg cagactctgg cctcggacag accagacatc     180
tacaacatgt tcttgttggc attggcggac atgcaaacca gcaaggcgga gaccgacccg     240
ctctcttact accagatctc tggtatccac ggagtcccct tcattccgtg gcaggagacg     300
tcggttagca cgcaggacac cagcacggga tactgcactc acaactctgt gctgttcgcc     360
acatggcaca gaccctacct ggccctcttc gaggagcgcc tggtgaagca tgccatctac     420
gttgcttcca agttcacggg aagccaggcc tccagatgga gtctgcggc caagaacgtt     480 cgtctgccgt actgggactg ggccgctacc gaccttcagg cccgtcttcc ccctcagctt     540
aaggctacta ccgttactgt cactcgccct ggtgccggag gtgttccgga gaccgtcacc     600
atcaacaacc cgctccgtca gtaccagttc cgtgacgcca acctgagaca gcagtacttc     660
gagttccagt tcaccgacgc cgctttcacc cgccgccagc tccggattc gtcgctgttg     720 tccagcaaca acgccgccgt cgatgccgcc atgaaccgtg actacaccag ccgcaggtcc     780
gccacctaca acttgttcag cattcccgac ttcagcgact tctcgggaac catgcgcaac     840
accaacggat cccccaatgc ttggaacagt gttgagtcgg tccacaacgg tgtccacgtt     900
aactgcggtg gacagtgggg ccacatgacc gcggttgcct actctgcttt cgatcccgtc     960
ttctggatgc accactgcaa cattgaccgt ctcatcgcca tgtaccaggc cactcaccct    1020
ggcagcgtgg tccagcctcg ccctgcttcc ggtaacttcg ctcgccaggt gaccgccaac    1080
gacctcgaca acattgacac tccgctggcg cctttccgtc accccgacgg caagtactac    1140
acctcccgag atgtctccgc tgtggactcc atctgggatt tcggttacca gtacactgag    1200
gttccgtttt cctaccgtgg caaccccctcc ggcctctctg cgttcaccac ccagcagatc    1260
aacgcgctgt accgcgacgg cagctcgtcc agccggaagc gtgatggtgc ttacaagcgc    1320
cgtgagtgga tctgccatat gacctacaac aacaacgagc ttccttccac ctcgtcgatc    1380
gagatctact tcgacaagcc tgccgagcaa gctccctcca gcactggctc catccccaag    1440
cccactgacg ctcccaagta ccgcaacggc acctacaccc gtcttcctc tcttagcgac    1500 gatgctttct actgtggatc tgcctccacg ctgcgtgacc ccaccgccaa gcacatgatg    1560
accatgaacg tcactggtgc cgtctacatg accgatgccc ttctggaggc tggctgccct    1620
```

```
tcgttggagc caaggatgt cgttcccttc ctcaagtcgc gcctgaagtg ggttgtccgc   1680
gtcggcggtg cggaggagta ccctctggag aagattcctt ccctgaaggt cggtgtttcg   1740
tcttcggatg tcgactaccc tgccgaggac accaagctcc ccacctgggg tatcttcgag   1800
acccactacg acatcaccga tctcaagctg tgcggtttca ccctggcgga caagggactc   1860
gtcgactctg tcgttgcccc catcgtcgac accgtctcct cggtcgtttc cgacatcgtt   1920
ggacaccttc ccactggctt gcccaccgac ctgcctctct cggcggttc tccttcgtcc    1980 tcttgcaccg aggagtcggc tgccgccact gacgctcctg agtactttt ccaccgacct    2040 gactcccaca tcgactga                                                 2058
```

<210> SEQ ID NO 2
<211> LENGTH: 685
<212> TYPE: PRT
<213> ORGANISM: Trichophaea saccata

<400> SEQUENCE: 2

```
Met Lys Phe Ser Ala Phe Val Ala Val Ala Thr Thr Ser Val Val Ala
1               5                   10                  15

Leu Leu Ser Gly Ser Val Glu Ala Gln Pro Val Pro Asn Phe Tyr
            20                  25                  30

Pro Val Arg Gly Ala Ile Ala Trp Thr Asn Ser Val Val Arg Arg Leu
        35                  40                  45

Pro Leu Gln Thr Leu Ala Ser Asp Arg Pro Asp Ile Tyr Asn Met Phe
    50                  55                  60

Leu Leu Ala Leu Ala Asp Met Gln Thr Ser Lys Ala Glu Thr Asp Pro
65                  70                  75                  80

Leu Ser Tyr Tyr Gln Ile Ser Gly Ile His Gly Val Pro Phe Ile Pro
                85                  90                  95

Trp Gln Glu Thr Ser Val Ser Thr Gln Asp Thr Ser Thr Gly Tyr Cys
            100                 105                 110

Thr His Asn Ser Val Leu Phe Ala Thr Trp His Arg Pro Tyr Leu Ala
        115                 120                 125

Leu Phe Glu Glu Arg Leu Val Lys His Ala Ile Tyr Val Ala Ser Lys
    130                 135                 140

Phe Thr Gly Ser Gln Ala Ser Arg Trp Gln Ser Ala Ala Lys Asn Val
145                 150                 155                 160

Arg Leu Pro Tyr Trp Asp Trp Ala Ala Thr Asp Leu Gln Ala Arg Leu
                165                 170                 175

Pro Pro Gln Leu Lys Ala Thr Thr Val Thr Val Thr Arg Pro Gly Ala
            180                 185                 190

Gly Gly Val Pro Glu Thr Val Thr Ile Asn Asn Pro Leu Arg Gln Tyr
        195                 200                 205

Gln Phe Arg Asp Ala Asn Leu Arg Gln Gln Tyr Phe Glu Phe Gln Phe
    210                 215                 220

Thr Asp Ala Ala Phe Thr Arg Arg Gln Pro Pro Asp Ser Ser Leu Leu
225                 230                 235                 240

Ser Ser Asn Asn Ala Ala Val Asp Ala Met Asn Arg Asp Tyr Thr
                245                 250                 255

Ser Arg Arg Ser Ala Thr Tyr Asn Leu Phe Ser Ile Pro Asp Phe Ser
                260                 265                 270

Asp Phe Ser Gly Thr Met Arg Asn Thr Asn Gly Ser Pro Asn Ala Trp
        275                 280                 285

Asn Ser Val Glu Ser Val His Asn Gly Val His Val Asn Cys Gly Gly
```

```
                290                 295                 300
Gln Trp Gly His Met Thr Ala Val Ala Tyr Ser Ala Phe Asp Pro Val
305                 310                 315                 320

Phe Trp Met His His Cys Asn Ile Asp Arg Leu Ile Ala Met Tyr Gln
                325                 330                 335

Ala Thr His Pro Gly Ser Val Val Gln Pro Arg Pro Ala Ser Gly Asn
                340                 345                 350

Phe Ala Arg Gln Val Thr Ala Asn Asp Leu Asp Asn Ile Asp Thr Pro
            355                 360                 365

Leu Ala Pro Phe Arg His Pro Asp Gly Lys Tyr Tyr Thr Ser Arg Asp
370                 375                 380

Val Ser Ala Val Asp Ser Ile Trp Asp Phe Gly Tyr Gln Tyr Thr Glu
385                 390                 395                 400

Val Pro Val Ser Tyr Arg Gly Asn Pro Ser Gly Leu Ser Ala Phe Thr
                405                 410                 415

Thr Gln Gln Ile Asn Ala Leu Tyr Arg Asp Gly Ser Ser Ser Ser Arg
                420                 425                 430

Lys Arg Asp Gly Ala Tyr Lys Arg Arg Glu Trp Ile Cys His Met Thr
            435                 440                 445

Tyr Asn Asn Asn Glu Leu Pro Ser Thr Ser Ser Ile Glu Ile Tyr Phe
450                 455                 460

Asp Lys Pro Ala Glu Gln Ala Pro Ser Ser Thr Gly Ser Ile Pro Lys
465                 470                 475                 480

Pro Thr Asp Ala Pro Lys Tyr Arg Asn Gly Thr Tyr Thr Pro Ser Ser
                485                 490                 495

Ser Leu Ser Asp Asp Ala Phe Tyr Cys Gly Ser Ala Ser Thr Leu Arg
                500                 505                 510

Asp Pro Thr Ala Lys His Met Met Thr Met Asn Val Thr Gly Ala Val
            515                 520                 525

Tyr Met Thr Asp Ala Leu Leu Glu Ala Gly Cys Pro Ser Leu Glu Pro
530                 535                 540

Lys Asp Val Val Pro Phe Leu Lys Ser Arg Leu Lys Trp Val Val Arg
545                 550                 555                 560

Val Gly Gly Ala Glu Glu Tyr Pro Leu Glu Lys Ile Pro Ser Leu Lys
                565                 570                 575

Val Gly Val Ser Ser Asp Val Asp Tyr Pro Ala Glu Asp Thr Lys
                580                 585                 590

Leu Pro Thr Trp Gly Ile Phe Glu Thr His Tyr Asp Ile Thr Asp Leu
            595                 600                 605

Lys Leu Cys Gly Phe Thr Leu Ala Asp Lys Gly Leu Val Asp Ser Val
610                 615                 620

Val Ala Pro Ile Val Asp Thr Val Ser Ser Val Ser Asp Ile Val
625                 630                 635                 640

Gly His Leu Pro Thr Gly Leu Pro Thr Asp Leu Pro Leu Phe Gly Gly
                645                 650                 655

Ser Pro Ser Ser Ser Cys Thr Glu Glu Ser Ala Ala Ala Thr Asp Ala
                660                 665                 670

Pro Glu Tyr Phe Phe His Arg Pro Asp Ser His Ile Asp
            675                 680                 685

<210> SEQ ID NO 3
<211> LENGTH: 34
<212> TYPE: DNA
<213> ORGANISM: Trichophaea saccata
```

-continued

```
<400> SEQUENCE: 3
tcgcgatccg ttttcgcatt tatcgtgaaa cgct                              34

<210> SEQ ID NO 4
<211> LENGTH: 33
<212> TYPE: DNA
<213> ORGANISM: Artificial
<220> FEATURE:
<223> OTHER INFORMATION: Primer

<400> SEQUENCE: 4
ccgcaaacgc tggtgaaagt aaaagatgct gaa                               33

<210> SEQ ID NO 5
<211> LENGTH: 20
<212> TYPE: DNA
<213> ORGANISM: Artificial
<220> FEATURE:
<223> OTHER INFORMATION: Primer

<400> SEQUENCE: 5
agcgtttgcg gccgcgatcc                                              20

<210> SEQ ID NO 6
<211> LENGTH: 20
<212> TYPE: DNA
<213> ORGANISM: Artificial
<220> FEATURE:
<223> OTHER INFORMATION: Primer

<400> SEQUENCE: 6
ttattcggtc gaaaaggatc                                              20

<210> SEQ ID NO 7
<211> LENGTH: 35
<212> TYPE: DNA
<213> ORGANISM: Artificial
<220> FEATURE:
<223> OTHER INFORMATION: Primer

<400> SEQUENCE: 7
gcggaattca ccatgaagtt ttcagccttt gtggc                             35

<210> SEQ ID NO 8
<211> LENGTH: 38
<212> TYPE: DNA
<213> ORGANISM: Artificial
<220> FEATURE:
<223> OTHER INFORMATION: Primer

<400> SEQUENCE: 8
atatgcggcc gcaggagtgg aggtaggggt gtagaccg                          38

<210> SEQ ID NO 9
<211> LENGTH: 21
<212> TYPE: DNA
<213> ORGANISM: Artificial
<220> FEATURE:
<223> OTHER INFORMATION: Primer

<400> SEQUENCE: 9
gtttccaact caatttacct c                                            21

<210> SEQ ID NO 10
<211> LENGTH: 21
<212> TYPE: DNA
```

<213> ORGANISM: Artificial
<220> FEATURE:
<223> OTHER INFORMATION: Primer

<400> SEQUENCE: 10
ttgccctcat ccccatcctt t                                              21

<210> SEQ ID NO 11
<211> LENGTH: 21
<212> TYPE: DNA
<213> ORGANISM: Artificial
<220> FEATURE:
<223> OTHER INFORMATION: Primer

<400> SEQUENCE: 11
ttgccctcat ccccatcctt t                                              21

<210> SEQ ID NO 12
<211> LENGTH: 4
<212> TYPE: PRT
<213> ORGANISM: Artificial
<220> FEATURE:
<223> OTHER INFORMATION: Synthetic construct
<220> FEATURE:
<221> NAME/KEY: misc_feature
<222> LOCATION: (2)..(2)
<223> OTHER INFORMATION: Xaa is Asp or Glu

<400> SEQUENCE: 12

Ile Xaa Gly Arg
1

<210> SEQ ID NO 13
<211> LENGTH: 5
<212> TYPE: PRT
<213> ORGANISM: Artificial
<220> FEATURE:
<223> OTHER INFORMATION: Synthetic construct

<400> SEQUENCE: 13

Asp Asp Asp Asp Lys
1               5

<210> SEQ ID NO 14
<211> LENGTH: 6
<212> TYPE: PRT
<213> ORGANISM: Artificial
<220> FEATURE:
<223> OTHER INFORMATION: Synthetic construct

<400> SEQUENCE: 14

Leu Val Pro Arg Gly Ser
1               5

<210> SEQ ID NO 15
<211> LENGTH: 7
<212> TYPE: PRT
<213> ORGANISM: Artificial
<220> FEATURE:
<223> OTHER INFORMATION: Synthetic construct

<400> SEQUENCE: 15

Glu Asn Leu Tyr Phe Gln Gly
1               5

<210> SEQ ID NO 16
<211> LENGTH: 8
<212> TYPE: PRT

```
-continued
<213> ORGANISM: Artificial
<220> FEATURE:
<223> OTHER INFORMATION: Synthetic construct

<400> SEQUENCE: 16

Leu Glu Val Leu Phe Gln Gly Pro
1               5
```

POLYPEPTIDE HAVING TYROSINASE ACTIVITY

CROSS-REFERENCE TO RELATED APPLICATIONS

This application is a 35 U.S.C. 371 national application of PCT/EP2010/053393 filed Mar. 16, 2010, which claims priority or the benefit under 35 U.S.C. 119 of European application no. 09155427.9 filed Mar. 17, 2009 and U.S. provisional application No. 61/161,087 filed Mar. 18, 2009, the contents of which are fully incorporated herein by reference.

REFERENCE TO A SEQUENCE LISTING

This application contains a Sequence Listing in computer readable form. The computer readable form is incorporated herein by reference.

REFERENCE TO A DEPOSIT OF BIOLOGICAL MATERIAL

This application contains a reference to a deposit of biological material, which deposit is incorporated herein by reference. For complete information see end of the description.

BACKGROUND OF THE INVENTION

1. Field of the Invention

The present invention relates to isolated polypeptides having tyrosinase activity and isolated polynucleotides encoding the polypeptides. The invention also relates to nucleic acid constructs, vectors, and host cells comprising the polynucleotides as well as methods of producing and using the polypeptides.

2. Description of the Related Art

Enzymatic protein modification is frequently used, e.g. in food processing. One purpose of such protein modification is improvement of texture of the food material. Texture is not only related to sensory perception, but also to stability, water holding capacity, gelling and emulsifying properties. Enzyme-aided structure engineering, e.g. via protein cross-linking, can therefore be exploited in several food applications, such as in meat, fish, dairy and cereal foods.

Enzymes having tyrosinase activity have previously been shown to be able to cross-link food proteins. Cross-linking may take place via the formation of o-quinones from protein-bound tyrosine. These o-quinones either condense with each other or react with free amino and sulfhydryl groups present in proteins.

Enzymes for industrial applications are preferably extracellular. Extracellular enzymes, such as secreted enzymes, are usually more stable and can more readily be produced in industrial scale by recombinant technology.

Enzymes having tyrosinase activity have previously been reported. See e.g. WO2006084953 disclosing extracellular tyrosinases obtainable from *Trichoderma* spp. and suggesting various uses of such tyrosinases. At least one of the *Trichoderma* spp. tyrosinases disclosed is proteolytically processed at its C-terminus, whereby about ⅓ of the protein is cleaved off. According to literature, fungal tyrosinases are activated in vivo by limited proteolytic cleavage (Decker, H. and Tuczek, F. (2000) Trends Biochem. Sci. 25, 392-397).

It is an object of the present invention to provide polypeptides having tyrosinase activity and polynucleotides encoding the polypeptides. Another object of the present invention is to provide polypeptides having tyrosinase activity which can be industrially produced in high amounts in a stable form. Another object of the present invention is to provide polypeptides having tyrosinase activity which have a higher specific activity as compared to known tyrosinases. Such polypeptides are useful in production of various food products, e.g. due to their ability to cross-link food proteins. Yet another object of the present invention is to provide methods for producing polypeptides having tyrosinase activity.

SUMMARY OF THE INVENTION

The present inventors have identified novel polypeptides having tyrosinase activity which can be recombinantly produced at high levels in a mature and stable form. Surprisingly, such polypeptides have a high specific activity when working on, e.g., milk proteins. Further, such polypeptides have a high specific activity at relatively low temperatures, which is advantageous in various industrial applications, e.g., for treatment of milk proteins, as the amount of oxygen in a protein-containing material to be modified by a polypeptide of the invention is generally higher at low temperature, and oxygen is utilized in the enzyme reaction. Therefore, a surprisingly small concentration of a polypeptide of the invention is sufficient for the enzyme to perform in various industrial applications, e.g., for stabilizing acidified milk drinks.

The present invention therefore relates to isolated polypeptides having tyrosinase activity selected from the group consisting of:

(a) a polypeptide comprising an amino acid sequence having preferably at least 60%, more preferably at least 65%, more preferably at least 70%, more preferably at least 75%, more preferably at least 80%, more preferably at least 85%, even more preferably at least 85%, most preferably at least 90%, and even most preferably at least 95% identity to the mature polypeptide of SEQ ID NO: 2;

(b) a polypeptide encoded by a polynucleotide that hybridizes under preferably at least low stringency conditions, more preferably at least medium stringency conditions, even more preferably at least medium-high stringency conditions, and most preferably at least high stringency conditions with (i) the mature polypeptide coding sequence of SEQ ID NO: 1, (ii) the genomic DNA sequence comprising the mature polypeptide coding sequence of SEQ ID NO: 1, or (iii) a full-length complementary strand of (i) or (ii);

(c) a polypeptide encoded by a polynucleotide comprising a nucleotide sequence having preferably at least 60%, more preferably at least 65%, more preferably at least 70%, more preferably at least 75%, more preferably at least 80%, more preferably at least 85%, even more preferably at least 85%, most preferably at least 90%, and even most preferably at least 95% identity to the mature polypeptide coding sequence of SEQ ID NO: 1; and (d) a variant comprising a substitution, deletion, and/or insertion of one or more (several) amino acids of the mature polypeptide of SEQ ID NO: 2.

The present invention also relates to isolated polynucleotides encoding polypeptides having tyrosinase activity, selected from the group consisting of:

(a) a polynucleotide encoding a polypeptide comprising an amino acid sequence having preferably at least 60%, more preferably at least 65%, more preferably at least 70%, more preferably at least 75%, more preferably at least 80%, more preferably at least 85%, even more preferably at least 85%, most preferably at least 90%, and even most preferably at least 95% identity to the mature polypeptide of SEQ ID NO: 2;

(b) a polynucleotide that hybridizes under preferably at least low stringency conditions, more preferably at least medium stringency conditions, even more preferably at least medium-high stringency conditions, and most preferably at least high stringency conditions with (i) the mature polypeptide coding sequence of SEQ ID NO: 1, (ii) the genomic DNA sequence comprising the mature polypeptide coding sequence of SEQ ID NO: 1, or (iii) a full-length complementary strand of (i) or (ii);

(c) a polynucleotide comprising a nucleotide sequence having preferably at least 60%, more preferably at least 65%, more preferably at least 70%, more preferably at least 75%, more preferably at least 80%, more preferably at least 85%, even more preferably at least 85%, most preferably at least 90%, and even most preferably at least 95% identity to the mature polypeptide coding sequence of SEQ ID NO: 1;

(d) a polynucleotide encoding a variant comprising a substitution, deletion, and/or insertion of one or more (several) amino acids of the mature polypeptide of SEQ ID NO: 2.

The present invention also relates to nucleic acid constructs, recombinant expression vectors, recombinant host cells comprising the polynucleotides, and methods of producing a polypeptide having tyrosinase activity.

The present invention also relates to methods of modifying a protein-containing material, wherein said material is contacted with a polypeptide of the invention.

DEFINITIONS

Tyrosinase activity: A tyrosinase according to the present invention is an enzyme which oxidizes tyrosine side chains in peptides/proteins and thereby possibly promotes crosslinking, e.g. to other peptides/proteins. A tyrosinase according to the invention may catalyze the o-hydroxylation of monophenols (phenol molecules in which the benzene ring contains a single hydroxyl substituent) to o-diphenols (phenol molecules containing two hydroxyl substituents) and further possibly catalyze the oxidation of o-diphenols to produce o-quinones.

For purposes of the present invention, tyrosinase activity may be determined by any method generally known in the art. L-Dopa or tyrosine can be used as a substrate, where after dopachrome formation may be monitored spectrophotometrically, or alternatively substrate consumption may be monitored by following the oxygen consumption. Tyrosinase activity can also be visualized on agar plates by adding an appropriate substrate such as tyrosine, whereby tyrosinase activity results in a dark zone around the colony.

Tyrosinase activity according to the present invention may be determined by incubating the enzyme with tyrosine or other monophenolic/diphenolic substrates in an appropriate buffer at various pH and temperatures e.g. 50 mM MES at pH 6.5 at 37° C. for 30 minutes and oxygen should be present during the reaction. Prosthetic groups can be added, e.g. $CuCl_2$, to ensure optimal enzyme activity. The enzymatic reaction can be stopped by heat treatment, e.g. 95° C., or extreme pH, e.g. below pH 2 or above pH 10, and the denatured state can be fixed by the addition of sodium EDTA (prevents refolding/reactivation). The enzymatic activity can be followed by spectrophotometric measurements at various wavelengths in the UV/Vis spectra, e.g. at 280 nm and 480 nm.

The polypeptides of the present invention have at least 20%, preferably at least 40%, more preferably at least 50%, more preferably at least 60%, more preferably at least 70%, more preferably at least 80%, even more preferably at least 90%, most preferably at least 95%, and even most preferably at least 100% of the tyrosinase activity of the mature polypeptide of SEQ ID NO: 2.

Isolated polypeptide: The term "isolated polypeptide" as used herein refers to a polypeptide that is isolated from a source. In a preferred aspect, the polypeptide is at least 1% pure, preferably at least 5% pure, more preferably at least 10% pure, more preferably at least 20% pure, more preferably at least 40% pure, more preferably at least 60% pure, even more preferably at least 80% pure, and most preferably at least 90% pure, as determined by SDS-PAGE.

Substantially pure polypeptide: The term "substantially pure polypeptide" denotes herein a polypeptide preparation that contains at most 10%, preferably at most 8%, more preferably at most 6%, more preferably at most 5%, more preferably at most 4%, more preferably at most 3%, even more preferably at most 2%, most preferably at most 1%, and even most preferably at most 0.5% by weight of other polypeptide material with which it is natively or recombinantly associated. It is, therefore, preferred that the substantially pure polypeptide is at least 92% pure, preferably at least 94% pure, more preferably at least 95% pure, more preferably at least 96% pure, more preferably at least 96% pure, more preferably at least 97% pure, more preferably at least 98% pure, even more preferably at least 99% pure, most preferably at least 99.5% pure, and even most preferably 100% pure by weight of the total polypeptide material present in the preparation. The polypeptides of the present invention are preferably in a substantially pure form, i.e., the polypeptide preparation is essentially free of other polypeptide material with which it is natively or recombinantly associated. This can be accomplished, for example, by preparing the polypeptide by well-known recombinant methods or by classical purification methods.

Mature polypeptide: The term "mature polypeptide" is defined herein as a polypeptide having tyrosinase activity that is in its final form following translation and any post-translational modifications, such as N-terminal processing, C-terminal truncation, glycosylation, phosphorylation, etc. In a preferred aspect, the mature polypeptide is amino acids 25 to 431 of SEQ ID NO: 2. This is based on the prediction program SignalP 3.0 (Jannick Dyrlov Bendtsen, Henrik Nielsen, Gunnar von Heijne and Soren Brunak (2004): Improved prediction of signal peptides: SignalP 3.0. *J. Mol. Biol.*, 340:783-795) that predicts amino acids 1 to 24 of SEQ ID NO: 2 to be a signal peptide. Further, LS-MS of a mature polypeptide according to the invention encoded by a polynucleotide having the sequence of SEQ ID NO: 1 has determined two amino acid sequences for the mature polypeptide, one consisting of amino acids 25 to 431 of SEQ ID NO: 2, and the other one consisting of amino acids 25 to 432 of SEQ ID NO: 2. This shows that both the N-terminal signal peptide and a C-terminal domain are cleaved off during maturation.

Mature polypeptide coding sequence: The term "mature polypeptide coding sequence" is defined herein as a nucleotide sequence that encodes a mature polypeptide having tyrosinase activity. In a preferred aspect, the mature polypeptide coding sequence is nucleotides 73 to 1293 of SEQ ID NO: 1 based on (i) the SignalP 3.0 program that predicts nucleotides 1 to 72 of SEQ ID NO: 1 encode a signal peptide, and (ii) the LS-MS data for the mature polypeptide summarized above.

Identity: The relatedness between two amino acid sequences or between two nucleotide sequences is described by the parameter "identity".

For purposes of the present invention, the degree of identity between two amino acid sequences is determined using the Needleman-Wunsch algorithm (Needleman and Wunsch, 1970, *J. Mol. Biol.* 48: 443-453) as implemented in the Needle program of the EMBOSS package (EMBOSS: The European Molecular Biology Open Software Suite, Rice et al., 2000, *Trends in Genetics* 16: 276-277), preferably version 3.0.0 or later. The optional parameters used are gap open penalty of 10, gap extension penalty of 0.5, and the EBLO-SUM62 (EMBOSS version of BLOSUM62) substitution matrix. The output of Needle labeled "longest identity" (obtained using the—nobrief option) is used as the percent identity and is calculated as follows:

(Identical Residues×100)/(Length of Alignment−Total Number of Gaps in Alignment)

For purposes of the present invention, the degree of identity between two deoxyribonucleotide sequences is determined using the Needleman-Wunsch algorithm (Needleman and Wunsch, 1970, supra) as implemented in the Needle program of the EMBOSS package (EMBOSS: The European Molecular Biology Open Software Suite, Rice et al., 2000, supra), preferably version 3.0.0 or later. The optional parameters used are gap open penalty of 10, gap extension penalty of 0.5, and the EDNAFULL (EMBOSS version of NCBI NUC4.4) substitution matrix. The output of Needle labeled "longest identity" (obtained using the—nobrief option) is used as the percent identity and is calculated as follows:

(Identical Deoxyribonucleotides×100)/(Length of Alignment−Total Number of Gaps in Alignment)

Homologous sequence: The term "homologous sequence" is defined herein as a predicted protein that gives an E value (or expectancy score) of less than 0.001 in a tfasty search (Pearson, W. R., 1999, in *Bioinformatics Methods and Protocols*, S. Misener and S. A. Krawetz, ed., pp. 185-219) with the tyrosinase from *Trichophaea saccata* (Accession No. DSM 21914).

Polypeptide fragment: The term "polypeptide fragment" is defined herein as a polypeptide having one or more (several) amino acids deleted from the amino and/or carboxyl terminus of the mature polypeptide of SEQ ID NO: 2; or a homologous sequence thereof; wherein the fragment has tyrosinase activity.

Subsequence: The term "subsequence" is defined herein as a nucleotide sequence having one or more (several) nucleotides deleted from the 5' and/or 3' end of the mature polypeptide coding sequence of SEQ ID NO: 1; or a homologous sequence thereof; wherein the subsequence encodes a polypeptide fragment having tyrosinase activity.

Allelic variant: The term "allelic variant" denotes herein any of two or more alternative forms of a gene occupying the same chromosomal locus. Allelic variation arises naturally through mutation, and may result in polymorphism within populations. Gene mutations can be silent (no change in the encoded polypeptide) or may encode polypeptides having altered amino acid sequences. An allelic variant of a polypeptide is a polypeptide encoded by an allelic variant of a gene.

Isolated polynucleotide: The term "isolated polynucleotide" as used herein refers to a polynucleotide that is isolated from a source. In a preferred aspect, the polynucleotide is at least 1% pure, preferably at least 5% pure, more preferably at least 10% pure, more preferably at least 20% pure, more preferably at least 40% pure, more preferably at least 60% pure, even more preferably at least 80% pure, and most preferably at least 90% pure, as determined by agarose electrophoresis.

Substantially pure polynucleotide: The term "substantially pure polynucleotide" as used herein refers to a polynucleotide preparation free of other extraneous or unwanted nucleotides and in a form suitable for use within genetically engineered protein production systems. Thus, a substantially pure polynucleotide contains at most 10%, preferably at most 8%, more preferably at most 6%, more preferably at most 5%, more preferably at most 4%, more preferably at most 3%, even more preferably at most 2%, most preferably at most 1%, and even most preferably at most 0.5% by weight of other polynucleotide material with which it is natively or recombinantly associated. A substantially pure polynucleotide may, however, include naturally occurring 5' and 3' untranslated regions, such as promoters and terminators. It is preferred that the substantially pure polynucleotide is at least 90% pure, preferably at least 92% pure, more preferably at least 94% pure, more preferably at least 95% pure, more preferably at least 96% pure, more preferably at least 97% pure, even more preferably at least 98% pure, most preferably at least 99%, and even most preferably at least 99.5% pure by weight. The polynucleotides of the present invention are preferably in a substantially pure form, i.e., the polynucleotide preparation is essentially free of other polynucleotide material with which it is natively or recombinantly associated. The polynucleotides may be of genomic, cDNA, RNA, semisynthetic, synthetic origin, or any combinations thereof.

Coding sequence: When used herein the term "coding sequence" means a nucleotide sequence, which directly specifies the amino acid sequence of its protein product. The boundaries of the coding sequence are generally determined by an open reading frame, which usually begins with the ATG start codon or alternative start codons such as GTG and TTG and ends with a stop codon such as TAA, TAG, and TGA. The coding sequence may be a DNA, cDNA, synthetic, or recombinant nucleotide sequence.

cDNA: The term "cDNA" is defined herein as a DNA molecule that can be prepared by reverse transcription from a mature, spliced, mRNA molecule obtained from a eukaryotic cell. cDNA lacks intron sequences that are usually present in the corresponding genomic DNA. The initial, primary RNA transcript is a precursor to mRNA that is processed through a series of steps before appearing as mature spliced mRNA. These steps include the removal of intron sequences by a process called splicing. cDNA derived from mRNA lacks, therefore, any intron sequences.

Nucleic acid construct: The term "nucleic acid construct" as used herein refers to a nucleic acid molecule, either single- or double-stranded, which is isolated from a naturally occurring gene or which is modified to contain segments of nucleic acids in a manner that would not otherwise exist in nature or which is synthetic. The term nucleic acid construct is synonymous with the term "expression cassette" when the nucleic acid construct contains the control sequences required for expression of a coding sequence of the present invention.

Control sequences: The term "control sequences" is defined herein to include all components necessary for the expression of a polynucleotide encoding a polypeptide of the present invention. Each control sequence may be native or foreign to the nucleotide sequence encoding the polypeptide or native or foreign to each other. Such control sequences include, but are not limited to, a leader, polyadenylation sequence, propeptide sequence, promoter, signal peptide sequence, and transcription terminator. At a minimum, the control sequences include a promoter, and transcriptional and translational stop signals. The control sequences may be provided with linkers for the purpose of introducing specific restriction sites facilitating ligation of the control sequences with the coding region of the nucleotide sequence encoding a polypeptide.

Operably linked: The term "operably linked" denotes herein a configuration in which a control sequence is placed at an appropriate position relative to the coding sequence of the polynucleotide sequence such that the control sequence directs the expression of the coding sequence of a polypeptide.

Expression: The term "expression" includes any step involved in the production of the polypeptide including, but not limited to, transcription, post-transcriptional modification, translation, post-translational modification, and secretion.

Expression vector: The term "expression vector" is defined herein as a linear or circular DNA molecule that comprises a polynucleotide encoding a polypeptide of the present invention and is operably linked to additional nucleotides that provide for its expression.

Host cell: The term "host cell", as used herein, includes any cell type that is susceptible to transformation, transfection, transduction, and the like with a nucleic acid construct or expression vector comprising a polynucleotide of the present invention.

Modification: The term "modification" means herein any chemical modification of the polypeptide consisting of the mature polypeptide of SEQ ID NO: 2; or a homologous sequence thereof; as well as genetic manipulation of the DNA encoding such a polypeptide. The modification can be a substitution, a deletion and/or an insertion of one or more (several) amino acids as well as replacements of one or more (several) amino acid side chains.

Artificial variant: When used herein, the term "artificial variant" means a polypeptide having tyrosinase activity produced by an organism expressing a modified polynucleotide sequence of the mature polypeptide coding sequence of SEQ ID NO: 1; or a homologous sequence thereof. The modified nucleotide sequence is obtained through human intervention by modification of the polynucleotide sequence disclosed in SEQ ID NO: 1; or a homologous sequence thereof.

DETAILED DESCRIPTION OF THE INVENTION

Polypeptides Having Tyrosinase Activity

In a first aspect, the present invention relates to isolated polypeptides comprising an amino acid sequence having a degree of identity to the mature polypeptide of SEQ ID NO: 2 of preferably at least 60%, more preferably at least 65%, more preferably at least 70%, more preferably at least 75%, more preferably at least 80%, more preferably at least 85%, even more preferably at least 90%, most preferably at least 95%, and even most preferably at least 96%, at least 97%, at least 98%, or at least 99%, which have tyrosinase activity (hereinafter "homologous polypeptides"). In a preferred aspect, the homologous polypeptides have an amino acid sequence that differs by ten amino acids, preferably by five amino acids, more preferably by four amino acids, even more preferably by three amino acids, most preferably by two amino acids, and even most preferably by one amino acid from the mature polypeptide of SEQ ID NO: 2.

A polypeptide of the present invention preferably comprises the amino acid sequence of SEQ ID NO: 2 or an allelic variant thereof; or a fragment thereof having tyrosinase activity. In a preferred aspect, the polypeptide comprises the amino acid sequence of SEQ ID NO: 2. In another preferred aspect, the polypeptide comprises the mature polypeptide of SEQ ID NO: 2. In another preferred aspect, the polypeptide comprises amino acids 25 to 431 of SEQ ID NO: 2, or an allelic variant thereof; or a fragment thereof having tyrosinase activity. In another preferred aspect, the polypeptide comprises amino acids 25 to 431 of SEQ ID NO: 2. In another preferred aspect, the polypeptide consists of the amino acid sequence of SEQ ID NO: 2 or an allelic variant thereof; or a fragment thereof having tyrosinase activity. In another preferred aspect, the polypeptide consists of the amino acid sequence of SEQ ID NO: 2. In another preferred aspect, the polypeptide consists of the mature polypeptide of SEQ ID NO: 2. In another preferred aspect, the polypeptide consists of amino acids 25 to 431 of SEQ ID NO: 2 or an allelic variant thereof; or a fragment thereof having tyrosinase activity. In another preferred aspect, the polypeptide consists of amino acids 25 to 431 of SEQ ID NO: 2. In another preferred aspect, the polypeptide consists of amino acids 25 to 432 of SEQ ID NO: 2 or an allelic variant thereof; or a fragment thereof having tyrosinase activity. In another preferred aspect, the polypeptide consists of amino acids 25 to 432 of SEQ ID NO: 2.

In a second aspect, the present invention relates to isolated polypeptides having tyrosinase activity that are encoded by polynucleotides that hybridize under preferably very low stringency conditions, more preferably low stringency conditions, more preferably medium stringency conditions, more preferably medium-high stringency conditions, even more preferably high stringency conditions, and most preferably very high stringency conditions with (i) the mature polypeptide coding sequence of SEQ ID NO: 1, (ii) the genomic DNA sequence comprising the mature polypeptide coding sequence of SEQ ID NO: 1, (iii) a subsequence of (i) or (ii), or (iv) a full-length complementary strand of (i), (ii), or (iii) (J. Sambrook, E. F. Fritsch, and T. Maniatis, 1989, *Molecular Cloning, A Laboratory Manual,* 2d edition, Cold Spring Harbor, N.Y.). A subsequence of the mature polypeptide coding sequence of SEQ ID NO: 1 contains at least 100 contiguous nucleotides or preferably at least 200 contiguous nucleotides. Moreover, the subsequence may encode a polypeptide fragment having tyrosinase activity. In a preferred aspect, the complementary strand is the full-length complementary strand of the mature polypeptide coding sequence of SEQ ID NO: 1.

The nucleotide sequence of SEQ ID NO: 1; or a subsequence thereof; as well as the amino acid sequence of SEQ ID NO: 2; or a fragment thereof; may be used to design nucleic acid probes to identify and clone DNA encoding polypeptides having tyrosinase activity from strains of different genera or species according to methods well known in the art. In particular, such probes can be used for hybridization with the genomic or cDNA of the genus or species of interest, following standard Southern blotting procedures, in order to identify and isolate the corresponding gene therein. Such probes can be considerably shorter than the entire sequence, but should be at least 14, preferably at least 25, more preferably at least 35, and most preferably at least 70 nucleotides in length. It is, however, preferred that the nucleic acid probe is at least 100 nucleotides in length. For example, the nucleic acid probe may be at least 200 nucleotides, preferably at least 300 nucleotides, more preferably at least 400 nucleotides, or most preferably at least 500 nucleotides in length. Even longer probes may be used, e.g., nucleic acid probes that are preferably at least 600 nucleotides, more preferably at least 700 nucleotides, even more preferably at least 800 nucleotides, or most preferably at least 900 nucleotides in length. Both DNA and RNA probes can be used. The probes are typically labeled for detecting the corresponding gene (for example, with $^{32}$P, $^{3}$H, $^{35}$S, biotin, or avidin). Such probes are encompassed by the present invention.

A genomic DNA or cDNA library prepared from such other strains may, therefore, be screened for DNA that hybridizes with the probes described above and encodes a polypeptide having tyrosinase activity. Genomic or other DNA from such other strains may be separated by agarose or polyacrylamide gel electrophoresis, or other separation techniques. DNA from the libraries or the separated DNA may be transferred to and immobilized on nitrocellulose or other suitable carrier material. In order to identify a clone or DNA that is homologous with SEQ ID NO: 1; or a subsequence thereof; the carrier material is preferably used in a Southern blot.

For purposes of the present invention, hybridization indicates that the nucleotide sequence hybridizes to a labeled nucleic acid probe corresponding to the mature polypeptide coding sequence of SEQ ID NO: 1; the genomic DNA sequence comprising the mature polypeptide coding sequence of SEQ ID NO: 1; its full-length complementary strand; or a subsequence thereof; under very low to very high stringency conditions. Molecules to which the nucleic acid probe hybridizes under these conditions can be detected using, for example, X-ray film.

In a preferred aspect, the nucleic acid probe is the mature polypeptide coding sequence of SEQ ID NO: 1. In another preferred aspect, the nucleic acid probe is nucleotides 73 to 1293 of SEQ ID NO: 1. In another preferred aspect, the nucleic acid probe is a polynucleotide sequence that encodes the polypeptide of SEQ ID NO: 2, or a subsequence thereof. In another preferred aspect, the nucleic acid probe is SEQ ID NO: 1. In another preferred aspect, the nucleic acid probe is the polynucleotide sequence contained in plasmid pXYZ1443 which is contained in E. coli DSM 21914, wherein the polynucleotide sequence thereof encodes a polypeptide having tyrosinase activity. In another preferred aspect, the nucleic acid probe is the mature polypeptide coding region contained in plasmid pXYZ1443 which is contained in E. coli DSM 21914.

For long probes of at least 100 nucleotides in length, very low to very high stringency conditions are defined as prehybridization and hybridization at 42° C. in 5×SSPE, 0.3% SDS, 200 µg/ml sheared and denatured salmon sperm DNA, and either 25% formamide for very low and low stringencies, 35% formamide for medium and medium-high stringencies, or 50% formamide for high and very high stringencies, following standard Southern blotting procedures for 12 to 24 hours optimally.

For long probes of at least 100 nucleotides in length, the carrier material is finally washed three times each for 15 minutes using 2×SSC, 0.2% SDS preferably at 45° C. (very low stringency), more preferably at 50° C. (low stringency), more preferably at 55° C. (medium stringency), more preferably at 60° C. (medium-high stringency), even more preferably at 65° C. (high stringency), and most preferably at 70° C. (very high stringency).

For short probes that are about 15 nucleotides to about 70 nucleotides in length, stringency conditions are defined as prehybridization, hybridization, and washing post-hybridization at about 5° C. to about 10° C. below the calculated $T_m$ using the calculation according to Bolton and McCarthy (1962, Proceedings of the National Academy of Sciences USA 48:1390) in 0.9 M NaCl, 0.09 M Tris-HCl pH 7.6, 6 mM EDTA, 0.5% NP-40, 1×Denhardt's solution, 1 mM sodium pyrophosphate, 1 mM sodium monobasic phosphate, 0.1 mM ATP, and 0.2 mg of yeast RNA per ml following standard Southern blotting procedures for 12 to 24 hours optimally.

For short probes that are about 15 nucleotides to about 70 nucleotides in length, the carrier material is washed once in 6×SCC plus 0.1% SDS for 15 minutes and twice each for 15 minutes using 6×SSC at 5° C. to 10° C. below the calculated $T_m$.

In a third aspect, the present invention relates to isolated polypeptides having tyrosinase activity encoded by polynucleotides comprising or consisting of nucleotide sequences that have a degree of identity to the mature polypeptide coding sequence of SEQ ID NO: 1 of preferably at least 60%, more preferably at least 65%, more preferably at least 70%, more preferably at least 75%, more preferably at least 80%, more preferably at least 85%, even more preferably at least 90%, most preferably at least 95%, and even most preferably 96%, 97%, 98%, or 99%, which encode an active polypeptide. See polynucleotide section herein.

In a fourth aspect, the present invention relates to artificial variants comprising a substitution, deletion, and/or insertion of one or more (or several) amino acids of the mature polypeptide of SEQ ID NO: 2; or a homologous sequence thereof. Preferably, amino acid changes are of a minor nature, that is conservative amino acid substitutions or insertions that do not significantly affect the folding and/or activity of the protein; small deletions, typically of one to about 30 amino acids; small amino- or carboxyl-terminal extensions, such as an amino-terminal methionine residue; a small linker peptide of up to about 20-25 residues; or a small extension that facilitates purification by changing net charge or another function, such as a poly-histidine tract, an antigenic epitope or a binding domain.

Examples of conservative substitutions are within the group of basic amino acids (arginine, lysine and histidine), acidic amino acids (glutamic acid and aspartic acid), polar amino acids (glutamine and asparagine), hydrophobic amino acids (leucine, isoleucine and valine), aromatic amino acids (phenylalanine, tryptophan and tyrosine), and small amino acids (glycine, alanine, serine, threonine and methionine). Amino acid substitutions that do not generally alter specific activity are known in the art and are described, for example, by H. Neurath and R. L. Hill, 1979, In, The Proteins, Academic Press, New York. The most commonly occurring exchanges are Ala/Ser, Val/Ile, Asp/Glu, Thr/Ser, Ala/Gly, Ala/Thr, Ser/Asn, Ala/Val, Ser/Gly, Tyr/Phe, Ala/Pro, Lys/Arg, Asp/Asn, Leu/Ile, Leu/Val, Ala/Glu, and Asp/Gly.

In addition to the 20 standard amino acids, non-standard amino acids (such as 4-hydroxyproline, 6-N-methyl lysine, 2-aminoisobutyric acid, isovaline, and alpha-methyl serine) may be substituted for amino acid residues of a wild-type polypeptide. A limited number of non-conservative amino acids, amino acids that are not encoded by the genetic code, and unnatural amino acids may be substituted for amino acid residues. "Unnatural amino acids" have been modified after protein synthesis, and/or have a chemical structure in their side chain(s) different from that of the standard amino acids. Unnatural amino acids can be chemically synthesized, and preferably, are commercially available, and include pipecolic acid, thiazolidine carboxylic acid, dehydroproline, 3- and 4-methylproline, and 3,3-dimethylproline.

Alternatively, the amino acid changes are of such a nature that the physico-chemical properties of the polypeptides are altered. For example, amino acid changes may improve the thermal stability of the polypeptide, alter the substrate specificity, change the pH optimum, and the like.

Essential amino acids in the parent polypeptide can be identified according to procedures known in the art, such as site-directed mutagenesis or alanine-scanning mutagenesis (Cunningham and Wells, 1989, Science 244: 1081-1085). In the latter technique, single alanine mutations are introduced at every residue in the molecule, and the resultant mutant molecules are tested for biological activity (i.e., tyrosinase activity) to identify amino acid residues that are critical to the activity of the molecule. See also, Hilton et al., 1996, J. Biol.

*Chem.* 271: 4699-4708. The active site of the enzyme or other biological interaction can also be determined by physical analysis of structure, as determined by such techniques as nuclear magnetic resonance, crystallography, electron diffraction, or photoaffinity labeling, in conjunction with mutation of putative contact site amino acids. See, for example, de Vos et al., 1992, *Science* 255: 306-312; Smith et al., 1992, *J. Mol. Biol.* 224: 899-904; Wlodaver et al., 1992, *FEBS Lett.* 309: 59-64. The identities of essential amino acids can also be inferred from analysis of identities with polypeptides that are related to a polypeptide according to the invention.

Single or multiple amino acid substitutions, deletions, and/or insertions can be made and tested using known methods of mutagenesis, recombination, and/or shuffling, followed by a relevant screening procedure, such as those disclosed by Reidhaar-Olson and Sauer, 1988, *Science* 241: 53-57; Bowie and Sauer, 1989, *Proc. Natl. Acad. Sci. USA* 86: 2152-2156; WO 95/17413; or WO 95/22625. Other methods that can be used include error-prone PCR, phage display (e.g., Lowman et al., 1991, *Biochem.* 30: 10832-10837; U.S. Pat. No. 5,223,409; WO 92/06204), and region-directed mutagenesis (Derbyshire et al., 1986, *Gene* 46: 145; Ner et al., 1988, *DNA* 7: 127).

Mutagenesis/shuffling methods can be combined with high-throughput, automated screening methods to detect activity of cloned, mutagenized polypeptides expressed by host cells (Ness et al., 1999, *Nature Biotechnology* 17: 893-896). Mutagenized DNA molecules that encode active polypeptides can be recovered from the host cells and rapidly sequenced using standard methods in the art. These methods allow the rapid determination of the importance of individual amino acid residues in a polypeptide of interest, and can be applied to polypeptides of unknown structure.

The total number of amino acid substitutions, deletions and/or insertions of the mature polypeptide of SEQ ID NO: 2, such as amino acids 25 to 431 of SEQ ID NO: 2, is 10, preferably 9, more preferably 8, more preferably 7, more preferably at most 6, more preferably 5, more preferably 4, even more preferably 3, most preferably 2, and even most preferably 1.

A polypeptide having tyrosinase activity is able to oxidize its own tyrosine residues which are accessible on the surface. These oxidized tyrosines (e.g. quinones) can make covalent crosslinks to other substance which can influence the activity of the polypeptide, e.g. if cross linked to another protein. Such auto-modification of a polypeptide having tyrosinase activity (caused by its own enzymatic activity) can also be made by tyrosinase oxidation of phenolic substances present in the solution. Such oxidized phenolic substances may react with surface accessible amino acid on the tyrosinase, e.g. solvent accessible lysine residues.

Therefore, especially Tyr and Lys, but also Cys, on the surface of a polypeptide having tyrosinase activity may be changed by site-directed mutagenesis. E.g., Tyr may be replaced with Ala, Cys, Asp, Glu, Phe, Gly, His, Ile, Lys, Leu, Met, Asn, Pro, Gln, Arg, Ser, Thr, Val, Trp; and Lys or Cys could be replace with Ala, Asp, Glu, Phe, Gly, His, Ile, Leu, Met, Asn, Pro, Gln, Arg, Ser, Thr, Val, Trp. Preferably, the tyrosine, lysine or cysteine residue to be modified is solvent accessible in the three-dimensional structure of the parent polypeptide.

In one aspect, the present invention therefore relates to an isolated polypeptide having tyrosinase activity, which:

(a) comprises an amino acid sequence having at least 60% identity to the mature polypeptide of SEQ ID NO: 2; and (b) comprises a different amino acid compared to SEQ ID NO: 2 in at least one of the positions where the amino acid of SEQ ID NO: 2 is tyrosine, lysine or cysteine.

Preferably, the amino acid sequence of such polypeptide has at least 60% or 70% identity, more preferably at least 80%, 90%, 95% or 98% identity, to the mature polypeptide of SEQ ID NO: 2.

Preferably, such polypeptide comprises a different amino acid compared to SEQ ID NO: 2 in at least one of the positions where the amino acid of SEQ ID NO: 2 is tyrosine. More preferably, such polypeptide comprises a different amino acid compared to SEQ ID NO: 2 in at least one of the positions where the amino acid of SEQ ID NO: 2 is a tyrosine which is solvent accessible when a polypeptide having the amino acid sequence of the mature polypeptide of SEQ ID NO: 2 is folded into its three-dimensional structure.

Sources of Polypeptides Having Tyrosinase Activity

A polypeptide of the present invention may be obtained from microorganisms of any genus. For purposes of the present invention, the term "obtained from" as used herein in connection with a given source shall mean that the polypeptide encoded by a nucleotide sequence is produced by the source or by a strain in which the nucleotide sequence from the source has been inserted. In a preferred aspect, the polypeptide obtained from a given source is secreted extracellularly.

A polypeptide having tyrosinase activity of the present invention may be a fungal polypeptide, and more preferably a yeast polypeptide such as a *Candida*, *Kluyveromyces*, *Pichia*, *Saccharomyces*, *Schizosaccharomyces*, or *Yarrowia* polypeptide having tyrosinase activity; or more preferably a filamentous fungal polypeptide such as an *Acremonium*, *Agaricus*, *Alternaria*, *Aspergillus*, *Aureobasidium*, *Botryospaeria*, *Ceriporiopsis*, *Chaetomidium*, *Chrysosporium*, *Claviceps*, *Cochliobolus*, *Coprinopsis*, *Coptotermes*, *Corynascus*, *Cryphonectria*, *Cryptococcus*, *Diplodia*, *Exidia*, *Filibasidium*, *Fusarium*, *Gibberella*, *Holomastigotoides*, *Humicola*, *Irpex*, *Lentinula*, *Leptospaeria*, *Magnaporthe*, *Melanocarpus*, *Meripilus*, *Mucor*, *Myceliophthora*, *Neocallimastix*, *Neurospora*, *Paecilomyces*, *Penicillium*, *Phanerochaete*, *Piromyces*, *Poitrasia*, *Pseudoplectania*, *Pseudotrichonympha*, *Rhizomucor*, *Schizophyllum*, *Scytalidium*, *Talaromyces*, *Thermoascus*, *Thielavia*, *Tolypocladium*, *Trichoderma*, *Trichophaea*, *Verticillium*, *Volvariella*, or *Xylaria* polypeptide having tyrosinase activity.

In a preferred aspect, the polypeptide is a *Saccharomyces carlsbergensis*, *Saccharomyces cerevisiae*, *Saccharomyces diastaticus*, *Saccharomyces douglasfi*, *Saccharomyces kluyveri*, *Saccharomyces norbensis*, or *Saccharomyces oviformis* polypeptide having tyrosinase activity.

In another preferred aspect, the polypeptide is an *Acremonium cellulolyticus*, *Aspergillus aculeatus*, *Aspergillus awamori*, *Aspergillus fumigatus*, *Aspergillus foetidus*, *Aspergillus japonicus*, *Aspergillus nidulans*, *Aspergillus niger*, *Aspergillus oryzae*, *Chrysosporium keratinophilum*, *Chrysosporium lucknowense*, *Chrysosporium tropicum*, *Chrysosporium merdarium*, *Chrysosporium inops*, *Chrysosporium pannicola*, *Chrysosporium queenslandicum*, *Chrysosporium zonatum*, *Fusarium bactridioides*, *Fusarium cerealis*, *Fusarium crookwellense*, *Fusarium culmorum*, *Fusarium graminearum*, *Fusarium graminum*, *Fusarium heterosporum*, *Fusarium negundi*, *Fusarium oxysporum*, *Fusarium reticulatum*, *Fusarium roseum*, *Fusarium sambucinum*, *Fusarium sarcochroum*, *Fusarium sporotrichioides*, *Fusarium sulphureum*, *Fusarium torulosum*, *Fusarium trichothecioides*, *Fusarium venenatum*, *Humicola grisea*, *Humicola insolens*, *Humicola lanuginosa*, *Irpex lacteus*, Mucor miehei, Myceliophthora thermophila, Neurospora crassa, Penicillium funiculosum, Penicillium purpurogenum, Phanerochaete chrysosporium, Thielavia achromatica, Thielavia albomyces, Thielavia albopilosa, Thielavia australeinsis, Thielavia fimeti, Thielavia microspora, Thielavia ovispora, Thielavia peruviana, Thielavia spededonium, Thielavia setosa, Thielavia subthermophila, Thielavia terrestris, Trichoderma harzianum, Trichoderma koningii, Trichoderma longibrachiatum, Trichoderma reesei, or Trichoderma viride polypeptide having having tyrosinase activity.

In a more preferred aspect, the polypeptide is a Trichophaea, preferabaly a Trichopheae saccata polypeptide having tyrosinase activity. In a most preferred aspect, the polypeptide is a Trichopheae saccata CBS804.70 polypeptide having tyrosinase activity, e.g., a polypeptide comprising the mature polypeptide of SEQ ID NO: 2.

It will be understood that for the aforementioned species the invention encompasses both the perfect and imperfect states, and other taxonomic equivalents, e.g., anamorphs, regardless of the species name by which they are known. Those skilled in the art will readily recognize the identity of appropriate equivalents.

Strains of these species are readily accessible to the public in a number of culture collections, such as the American Type Culture Collection (ATCC), Deutsche Sammlung von Mikroorganismen and Zellkulturen GmbH (DSM), Centraalbureau Voor Schimmelcultures (CBS), and Agricultural Research Service Patent Culture Collection, Northern Regional Research Center (NRRL).

Furthermore, such polypeptides may be identified and obtained from other sources including microorganisms isolated from nature (e.g., soil, composts, water, etc.) using the above-mentioned probes. Techniques for isolating microorganisms from natural habitats are well known in the art. The polynucleotide may then be obtained by similarly screening a genomic or cDNA library of such a microorganism. Once a polynucleotide sequence encoding a polypeptide has been detected with the probe(s), the polynucleotide can be isolated or cloned by utilizing techniques that are well known to those of ordinary skill in the art (see, e.g., Sambrook et al., 1989, supra).

Polypeptides of the present invention also include fused polypeptides or cleavable fusion polypeptides in which another polypeptide is fused at the N-terminus or the C-terminus of the polypeptide or fragment thereof. A fused polypeptide is produced by fusing a nucleotide sequence (or a portion thereof) encoding another polypeptide to a nucleotide sequence (or a portion thereof) of the present invention. Techniques for producing fusion polypeptides are known in the art, and include ligating the coding sequences encoding the polypeptides so that they are in frame and that expression of the fused polypeptide is under control of the same promoter(s) and terminator.

A fusion polypeptide can further comprise a cleavage site. Upon secretion of the fusion protein, the site is cleaved releasing the polypeptide having tyrosinase activity from the fusion protein. Examples of cleavage sites include, but are not limited to, a Kex2 site that encodes the dipeptide Lys-Arg (Martin et al., 2003, J. Ind. Microbiol. Biotechnol. 3: 568-76; Svetina et al., 2000, J. Biotechnol. 76: 245-251; Rasmussen-Wilson et al., 1997, Appl. Environ. Microbiol. 63: 3488-3493; Ward et al., 1995, Biotechnology 13: 498-503; and Contreras et al., 1991, Biotechnology 9: 378-381), an Ile-(Glu or Asp)-Gly-Arg (SEQ ID NO: 12) site, which is cleaved by a Factor Xa protease after the arginine residue (Eaton et al., 1986, Biochem. 25: 505-512); a Asp-Asp-Asp-Asp-Lys SEQ ID NO: 13) site, which is cleaved by an enterokinase after the lysine (Collins-Racie et al., 1995, Biotechnology 13: 982-987); a His-Tyr-Glu site or His-Tyr-Asp site, which is cleaved by Genenase I (Carter et al., 1989, Proteins: Structure, Function, and Genetics 6: 240-248); a Leu-Val-Pro-Arg-Gly-Ser (SEQ ID NO: 14) site, which is cleaved by thrombin after the Arg (Stevens, 2003, Drug Discovery World 4: 35-48); a Glu-Asn-Leu-Tyr-Phe-Gln-Gly (SEQ ID NO: 15) site, which is cleaved by TEV protease after the Gln (Stevens, 2003, supra); and a Leu-Glu-Val-Leu-Phe-Gln-Gly-Pro (SEQ ID NO: 16) site, which is cleaved by a genetically engineered form of human rhinovirus 3C protease after the Gln (Stevens, 2003, supra).

Polynucleotides

The present invention also relates to isolated polynucleotides comprising or consisting of nucleotide sequences that encode polypeptides having tyrosinase activity of the present invention.

In a preferred aspect, the nucleotide sequence comprises or consists of SEQ ID NO: 1. In another more preferred aspect, the nucleotide sequence comprises or consists of the tyrosinase encoding sequence contained in plasmid pXYZ1443 which is contained in E. coli DSM 21914. In another preferred aspect, the nucleotide sequence comprises or consists of the mature polypeptide coding sequence of SEQ ID NO: 1. In another preferred aspect, the nucleotide sequence comprises or consists of nucleotides 73 to 1293 of SEQ ID NO: 1. In another more preferred aspect, the nucleotide sequence comprises or consists of the mature polypeptide coding sequence contained in plasmid pXYZ1443 which is contained in E. coli DSM 21914. The present invention also encompasses nucleotide sequences that encode polypeptides comprising or consisting of the amino acid sequence of SEQ ID NO: 2 or the mature polypeptide thereof, which differ from SEQ ID NO: 1 or the mature polypeptide coding sequence thereof by virtue of the degeneracy of the genetic code. The present invention also relates to subsequences of SEQ ID NO: 1 that encode fragments of SEQ ID NO: 2 that have tyrosinase activity.

The present invention also relates to mutant polynucleotides comprising or consisting of at least one mutation in the mature polypeptide coding sequence of SEQ ID NO: 1, in which the mutant nucleotide sequence encodes the mature polypeptide of SEQ ID NO: 2.

The techniques used to isolate or clone a polynucleotide encoding a polypeptide are known in the art and include isolation from genomic DNA, preparation from cDNA, or a combination thereof. The cloning of the polynucleotides of the present invention from such genomic DNA can be effected, e.g., by using the well known polymerase chain reaction (PCR) or antibody screening of expression libraries to detect cloned DNA fragments with shared structural features. See, e.g., Innis et al., 1990, PCR: A Guide to Methods and Application, Academic Press, New York. Other nucleic acid amplification procedures such as ligase chain reaction (LCR), ligated activated transcription (LAT) and nucleotide sequence-based amplification (NASBA) may be used. The polynucleotides may be cloned from a strain of Trichophaea, or another or related organism and thus, for example, may be an allelic or species variant of the polypeptide encoding region of the nucleotide sequence.

The present invention also relates to isolated polynucleotides comprising or consisting of nucleotide sequences that have a degree of identity to the mature polypeptide coding sequence of SEQ ID NO: 1 of preferably at least 60%, more preferably at least 65%, more preferably at least 70%, more preferably at least 75%, more preferably at least 80%, more preferably at least 85%, even more preferably at least 90%, most preferably at least 95%, and even most preferably at least 96%, at least 97%, at least 98%, or at least 99% identity, which encode an active polypeptide.

Modification of a nucleotide sequence encoding a polypeptide of the present invention may be necessary for the synthesis of polypeptides substantially similar to the polypeptide. The term "substantially similar" to the polypeptide refers to non-naturally occurring forms of the polypeptide. These polypeptides may differ in some engineered way from the polypeptide isolated from its native source, e.g., artificial variants that differ in specific activity, thermostability, pH optimum, or the like. The variant sequence may be constructed on the basis of the nucleotide sequence presented as the mature polypeptide coding sequence of SEQ ID NO: 1, e.g., a subsequence thereof, and/or by introduction of nucleotide substitutions that do not give rise to another amino acid sequence of the polypeptide encoded by the nucleotide sequence, but which correspond to the codon usage of the host organism intended for production of the enzyme, or by introduction of nucleotide substitutions that may give rise to a different amino acid sequence. For a general description of nucleotide substitution, see, e.g., Ford et al., 1991, *Protein Expression and Purification* 2: 95-107.

It will be apparent to those skilled in the art that such substitutions can be made outside the regions critical to the function of the molecule and still result in an active polypeptide. Amino acid residues essential to the activity of the polypeptide encoded by an isolated polynucleotide of the invention, and therefore preferably not subject to substitution, may be identified according to procedures known in the art, such as site-directed mutagenesis or alanine-scanning mutagenesis (see, e.g., Cunningham and Wells, 1989, supra). In the latter technique, mutations are introduced at every positively charged residue in the molecule, and the resultant mutant molecules are tested for tyrosinase activity to identify amino acid residues that are critical to the activity of the molecule. Sites of substrate-enzyme interaction can also be determined by analysis of the three-dimensional structure as determined by such techniques as nuclear magnetic resonance analysis, crystallography or photoaffinity labeling (see, e.g., de Vos et al., 1992, supra; Smith et al., 1992, supra; Wlodaver et al., 1992, supra).

The present invention also relates to isolated polynucleotides encoding polypeptides of the present invention, which hybridize under very low stringency conditions, preferably low stringency conditions, more preferably medium stringency conditions, more preferably medium-high stringency conditions, even more preferably high stringency conditions, and most preferably very high stringency conditions with (i) the mature polypeptide coding sequence of SEQ ID NO: 1, (ii) the genomic DNA sequence comprising the mature polypeptide coding sequence of SEQ ID NO: 1, or (iii) a full-length complementary strand of (i) or (ii); or allelic variants and subsequences thereof (Sambrook et al., 1989, supra), as defined herein. In a preferred aspect, the complementary strand is the full-length complementary strand of the mature polypeptide coding sequence of SEQ ID NO: 1.

The present invention also relates to isolated polynucleotides obtained by (a) hybridizing a population of DNA under very low, low, medium, medium-high, high, or very high stringency conditions with (i) the mature polypeptide coding sequence of SEQ ID NO: 1, (ii) the genomic DNA sequence comprising the mature polypeptide coding sequence of SEQ ID NO: 1, or (iii) a full-length complementary strand of (i) or (ii); and (b) isolating the hybridizing polynucleotide, which encodes a polypeptide having tyrosinase activity. In a preferred aspect, the complementary strand is the full-length complementary strand of the mature polypeptide coding sequence of SEQ ID NO: 1.

Nucleic Acid Constructs

The present invention also relates to nucleic acid constructs comprising an isolated polynucleotide of the present invention operably linked to one or more (several) control sequences that direct the expression of the coding sequence in a suitable host cell under conditions compatible with the control sequences.

An isolated polynucleotide encoding a polypeptide of the present invention may be manipulated in a variety of ways to provide for expression of the polypeptide. Manipulation of the polynucleotide's sequence prior to its insertion into a vector may be desirable or necessary depending on the expression vector. The techniques for modifying polynucleotide sequences utilizing recombinant DNA methods are well known in the art.

The control sequence may be an appropriate promoter sequence, a nucleotide sequence that is recognized by a host cell for expression of a polynucleotide encoding a polypeptide of the present invention. The promoter sequence contains transcriptional control sequences that mediate the expression of the polypeptide. The promoter may be any nucleotide sequence that shows transcriptional activity in the host cell of choice including mutant, truncated, and hybrid promoters, and may be obtained from genes encoding extracellular or intracellular polypeptides either homologous or heterologous to the host cell.

Examples of suitable promoters for directing the transcription of the nucleic acid constructs of the present invention in a filamentous fungal host cell are promoters obtained from the genes for *Aspergillus oryzae* TAKA amylase, *Rhizomucor miehei* aspartic proteinase, *Aspergillus niger* neutral alpha-amylase, *Aspergillus niger* acid stable alpha-amylase, *Aspergillus niger* or *Aspergillus awamori* glucoamylase (glaA), *Rhizomucor miehei* lipase, *Aspergillus oryzae* alkaline protease, *Aspergillus oryzae* triose phosphate isomerase, *Aspergillus nidulans* acetamidase, *Fusarium venenatum* amyloglucosidase (WO 00/56900), *Fusarium venenatum* Dania (WO 00/56900), *Fusarium venenatum* Quinn (WO 00/56900), *Fusarium oxysporum* trypsin-like protease (WO 96/00787), *Trichoderma reesei* beta-glucosidase, *Trichoderma reesei* cellobiohydrolase I, *Trichoderma reesei* cellobiohydrolase II, *Trichoderma reesei* endoglucanase I, *Trichoderma reesei* endoglucanase II, *Trichoderma reesei* endoglucanase III, *Trichoderma reesei* endoglucanase IV, *Trichoderma reesei* endoglucanase V, *Trichoderma reesei* xylanase I, *Trichoderma reesei* xylanase II, *Trichoderma reesei* beta-xylosidase, as well as the NA2-tpi promoter (a hybrid of the promoters from the genes for *Aspergillus niger* neutral alpha-amylase and *Aspergillus oryzae* triose phosphate isomerase); and mutant, truncated, and hybrid promoters thereof.

In a yeast host, useful promoters are obtained from the genes for *Saccharomyces cerevisiae* enolase (ENO-1), *Saccharomyces cerevisiae* galactokinase (GAL1), *Saccharomyces cerevisiae* alcohol dehydrogenase/glyceraldehyde-3-phosphate dehydrogenase (ADH1, ADH2/GAP), *Saccharomyces cerevisiae* triose phosphate isomerase (TPI), *Saccharomyces cerevisiae* metallothionein (CUP1), and *Saccharomyces cerevisiae* 3-phosphoglycerate kinase. Other useful promoters for yeast host cells are described by Romanos et al., 1992, *Yeast* 8: 423-488.

The control sequence may also be a suitable transcription terminator sequence, a sequence recognized by a host cell to terminate transcription. The terminator sequence is operably linked to the 3' terminus of the nucleotide sequence encoding the polypeptide. Any terminator that is functional in the host cell of choice may be used in the present invention.

Preferred terminators for filamentous fungal host cells are obtained from the genes for *Aspergillus oryzae* TAKA amylase, *Aspergillus niger* glucoamylase, *Aspergillus nidulans* anthranilate synthase, *Aspergillus niger* alpha-glucosidase, and *Fusarium oxysporum* trypsin-like protease.

Preferred terminators for yeast host cells are obtained from the genes for *Saccharomyces cerevisiae* enolase, *Saccharomyces cerevisiae* cytochrome C (CYC1), and *Saccharomyces cerevisiae* glyceraldehyde-3-phosphate dehydrogenase. Other useful terminators for yeast host cells are described by Romanos et al., 1992, supra.

The control sequence may also be a suitable leader sequence, a nontranslated region of an mRNA that is important for translation by the host cell. The leader sequence is operably linked to the 5' terminus of the nucleotide sequence encoding the polypeptide. Any leader sequence that is functional in the host cell of choice may be used in the present invention.

Preferred leaders for filamentous fungal host cells are obtained from the genes for *Aspergillus oryzae* TAKA amylase and *Aspergillus nidulans* triose phosphate isomerase.

Suitable leaders for yeast host cells are obtained from the genes for *Saccharomyces cerevisiae* enolase (ENO-1), *Saccharomyces cerevisiae* 3-phosphoglycerate kinase, *Saccharomyces cerevisiae* alpha-factor, and *Saccharomyces cerevisiae* alcohol dehydrogenase/glyceraldehyde-3-phosphate dehydrogenase (ADH2/GAP).

The control sequence may also be a polyadenylation sequence, a sequence operably linked to the 3' terminus of the nucleotide sequence and, when transcribed, is recognized by the host cell as a signal to add polyadenosine residues to transcribed mRNA. Any polyadenylation sequence that is functional in the host cell of choice may be used in the present invention.

Preferred polyadenylation sequences for filamentous fungal host cells are obtained from the genes for *Aspergillus oryzae* TAKA amylase, *Aspergillus niger* glucoamylase, *Aspergillus nidulans* anthranilate synthase, *Fusarium oxysporum* trypsin-like protease, and *Aspergillus niger* alpha-glucosidase.

Useful polyadenylation sequences for yeast host cells are described by Guo and Sherman, 1995, *Molecular Cellular Biology* 15: 5983-5990.

The control sequence may also be a signal peptide coding sequence that codes for an amino acid sequence linked to the amino terminus of a polypeptide and directs the encoded polypeptide into the cell's secretory pathway. The 5' end of the coding sequence of the nucleotide sequence may inherently contain a signal peptide coding sequence naturally linked in translation reading frame with the segment of the coding sequence that encodes the secreted polypeptide. Alternatively, the 5' end of the coding sequence may contain a signal peptide coding sequence that is foreign to the coding sequence. The foreign signal peptide coding sequence may be required where the coding sequence does not naturally contain a signal peptide coding sequence. Alternatively, the foreign signal peptide coding sequence may simply replace the natural signal peptide coding sequence in order to enhance secretion of the polypeptide. However, any signal peptide coding sequence that directs the expressed polypeptide into the secretory pathway of a host cell of choice, i.e., secreted into a culture medium, may be used in the present invention.

Effective signal peptide coding sequences for filamentous fungal host cells are the signal peptide coding sequences obtained from the genes for *Aspergillus oryzae* TAKA amylase, *Aspergillus niger* neutral amylase, *Aspergillus niger* glucoamylase, *Rhizomucor miehei* aspartic proteinase, *Humicola insolens* cellulase, *Humicola insolens* endoglucanase V, and *Humicola lanuginosa* lipase.

Useful signal peptides for yeast host cells are obtained from the genes for *Saccharomyces cerevisiae* alpha-factor and *Saccharomyces cerevisiae* invertase. Other useful signal peptide coding sequences are described by Romanos et al., 1992, supra.

In a preferred aspect, the signal peptide comprises or consists of amino acids 1 to 24 of SEQ ID NO: 2. In another preferred aspect, the signal peptide coding sequence comprises or consists of nucleotides 1 to 72 of SEQ ID NO: 1.

The control sequence may also be a propeptide coding sequence that codes for an amino acid sequence positioned at the amino terminus of a polypeptide. The resultant polypeptide is known as a proenzyme or propolypeptide (or a zymogen in some cases). A propeptide is generally inactive and can be converted to a mature active polypeptide by catalytic or autocatalytic cleavage of the propeptide from the propolypeptide. The propeptide coding sequence may be obtained from the genes for *Saccharomyces cerevisiae* alpha-factor, *Rhizomucor miehei* aspartic proteinase, and *Myceliophthora thermophila* laccase (WO 95/33836).

Where both signal peptide and propeptide sequences are present at the amino terminus of a polypeptide, the propeptide sequence is positioned next to the amino terminus of a polypeptide and the signal peptide sequence is positioned next to the amino terminus of the propeptide sequence.

It may also be desirable to add regulatory sequences that allow the regulation of the expression of the polypeptide relative to the growth of the host cell. Examples of regulatory systems are those that cause the expression of the gene to be turned on or off in response to a chemical or physical stimulus, including the presence of a regulatory compound. Regulatory systems in yeast systems include the ADH2 system or GAL1 system. In filamentous fungi, the TAKA alpha-amylase promoter, *Aspergillus niger* glucoamylase promoter, and *Aspergillus oryzae* glucoamylase promoter may be used as regulatory sequences. Other examples of regulatory sequences are those that allow for gene amplification. In eukaryotic systems, these regulatory sequences include the dihydrofolate reductase gene that is amplified in the presence of methotrexate, and the metallothionein genes that are amplified with heavy metals. In these cases, the nucleotide sequence encoding the polypeptide would be operably linked with the regulatory sequence.

Expression Vectors

The present invention also relates to recombinant expression vectors comprising a polynucleotide of the present invention, a promoter, and transcriptional and translational stop signals. The various nucleic acids and control sequences described herein may be joined together to produce a recombinant expression vector that may include one or more (several) convenient restriction sites to allow for insertion or substitution of the nucleotide sequence encoding the polypeptide at such sites. Alternatively, a polynucleotide sequence of the present invention may be expressed by inserting the nucleotide sequence or a nucleic acid construct comprising the sequence into an appropriate vector for expression. In creating the expression vector, the coding sequence is located in the vector so that the coding sequence is operably linked with the appropriate control sequences for expression.

The recombinant expression vector may be any vector (e.g., a plasmid or virus) that can be conveniently subjected to recombinant DNA procedures and can bring about expression of the nucleotide sequence. The choice of the vector will typically depend on the compatibility of the vector with the host cell into which the vector is to be introduced. The vectors may be linear or closed circular plasmids.

The vector may be an autonomously replicating vector, i.e., a vector that exists as an extrachromosomal entity, the replication of which is independent of chromosomal replication, e.g., a plasmid, an extrachromosomal element, a minichromosome, or an artificial chromosome. The vector may contain any means for assuring self-replication. Alternatively, the vector may be one that, when introduced into the host cell, is integrated into the genome and replicated together with the chromosome(s) into which it has been integrated. Furthermore, a single vector or plasmid or two or more vectors or plasmids that together contain the total DNA to be introduced into the genome of the host cell, or a transposon, may be used.

The vectors of the present invention preferably contain one or more (several) selectable markers that permit easy selection of transformed, transfected, transduced, or the like cells. A selectable marker is a gene the product of which provides for biocide or viral resistance, resistance to heavy metals, prototrophy to auxotrophs, and the like.

Suitable markers for yeast host cells are ADE2, HIS3, LEU2, LYS2, MET3, TRP1, and URA3. Selectable markers for use in a filamentous fungal host cell include, but are not limited to, amdS (acetamidase), argB (ornithine carbamoyltransferase), bar (phosphinothricin acetyltransferase), hph (hygromycin phosphotransferase), niaD (nitrate reductase), pyrG (orotidine-5'-phosphate decarboxylase), sC (sulfate adenyltransferase), and trpC (anthranilate synthase), as well as equivalents thereof. Preferred for use in an *Aspergillus* cell are the amdS and pyrG genes of *Aspergillus nidulans* or *Aspergillus oryzae* and the bar gene of *Streptomyces hygroscopicus*.

The vectors of the present invention preferably contain an element(s) that permits integration of the vector into the host cell's genome or autonomous replication of the vector in the cell independent of the genome.

For integration into the host cell genome, the vector may rely on the polynucleotide's sequence encoding the polypeptide or any other element of the vector for integration into the genome by homologous or nonhomologous recombination. Alternatively, the vector may contain additional nucleotide sequences for directing integration by homologous recombination into the genome of the host cell at a precise location(s) in the chromosome(s). To increase the likelihood of integration at a precise location, the integrational elements should preferably contain a sufficient number of nucleic acids, such as 100 to 10,000 base pairs, preferably 400 to 10,000 base pairs, and most preferably 800 to 10,000 base pairs, which have a high degree of identity to the corresponding target sequence to enhance the probability of homologous recombination. The integrational elements may be any sequence that is homologous with the target sequence in the genome of the host cell. Furthermore, the integrational elements may be non-encoding or encoding nucleotide sequences. On the other hand, the vector may be integrated into the genome of the host cell by non-homologous recombination.

For autonomous replication, the vector may further comprise an origin of replication enabling the vector to replicate autonomously in the host cell in question. The origin of replication may be any plasmid replicator mediating autonomous replication that functions in a cell. The term "origin of replication" or "plasmid replicator" is defined herein as a nucleotide sequence that enables a plasmid or vector to replicate in vivo.

Examples of origins of replication for use in a yeast host cell are the 2 micron origin of replication, ARS1, ARS4, the combination of ARS1 and CEN3, and the combination of ARS4 and CEN6.

Examples of origins of replication useful in a filamentous fungal cell are AMA1 and ANSI (Gems et al., 1991, *Gene* 98: 61-67; Cullen et al., 1987, *Nucleic Acids Research* 15: 9163-9175; WO 00/24883). Isolation of the AMA1 gene and construction of plasmids or vectors comprising the gene can be accomplished according to the methods disclosed in WO 00/24883.

More than one copy of a polynucleotide of the present invention may be inserted into a host cell to increase production of the gene product. An increase in the copy number of the polynucleotide can be obtained by integrating at least one additional copy of the sequence into the host cell genome or by including an amplifiable selectable marker gene with the polynucleotide where cells containing amplified copies of the selectable marker gene, and thereby additional copies of the polynucleotide, can be selected for by cultivating the cells in the presence of the appropriate selectable agent.

The procedures used to ligate the elements described above to construct the recombinant expression vectors of the present invention are well known to one skilled in the art (see, e.g., Sambrook et al., 1989, supra).

Host Cells

The present invention also relates to recombinant host cells, comprising an isolated polynucleotide of the present invention, which are advantageously used in the recombinant production of the polypeptides. A vector comprising a polynucleotide of the present invention is introduced into a host cell so that the vector is maintained as a chromosomal integrant or as a self-replicating extra-chromosomal vector as described earlier. The term "host cell" encompasses any progeny of a parent cell that is not identical to the parent cell due to mutations that occur during replication. The choice of a host cell will to a large extent depend upon the gene encoding the polypeptide and its source.

The host cell may be any cell useful in the recombinant production of a polypeptide of the present invention, e.g., a prokaryote or a eukaryote, such as a mammalian, insect, plant, or fungal cell.

In a preferred aspect, the host cell is a fungal cell. "Fungi" as used herein includes the phyla Ascomycota, Basidiomycota, Chytridiomycota, and Zygomycota (as defined by Hawksworth et al., In, *Ainsworth and Bisby's Dictionary of The Fungi,* 8th edition, 1995, CAB International, University Press, Cambridge, UK) as well as the Oomycota (as cited in Hawksworth et al., 1995, supra, page 171) and all mitosporic fungi (Hawksworth et al., 1995, supra).

In a more preferred aspect, the fungal host cell is a yeast cell. "Yeast" as used herein includes ascosporogenous yeast (Endomycetales), basidiosporogenous yeast, and yeast belonging to the Fungi Imperfecti (Blastomycetes). Since the classification of yeast may change in the future, for the purposes of this invention, yeast shall be defined as described in Biology and Activities of Yeast (Skinner, F. A., Passmore, S. M., and Davenport, R. R., eds, *Soc. App. Bacteriol. Symposium Series* No. 9, 1980).

In an even more preferred aspect, the yeast host cell is a *Candida, Hansenula, Kluyveromyces, Pichia, Saccharomyces, Schizosaccharomyces,* or *Yarrowia* cell.

In a most preferred aspect, the yeast host cell is a *Saccharomyces carlsbergensis, Saccharomyces cerevisiae, Saccharomyces diastaticus, Saccharomyces douglasii, Saccharomyces kluyveri, Saccharomyces norbensis,* or *Saccharomyces oviformis* cell. In another most preferred aspect, the yeast host cell is a *Kluyveromyces lactis* cell. In another most preferred aspect, the yeast host cell is a *Yarrowia lipolytica* cell.

In another more preferred aspect, the fungal host cell is a filamentous fungal cell. "Filamentous fungi" include all filamentous forms of the subdivision Eumycota and Oomycota (as defined by Hawksworth et al., 1995, supra). The filamentous fungi are generally characterized by a mycelial wall composed of chitin, cellulose, glucan, chitosan, mannan, and other complex polysaccharides. Vegetative growth is by hyphal elongation and carbon catabolism is obligately aerobic. In contrast, vegetative growth by yeasts such as *Saccharomyces cerevisiae* is by budding of a unicellular thallus and carbon catabolism may be fermentative.

In an even more preferred aspect, the filamentous fungal host cell is an *Acremonium, Aspergillus, Aureobasidium, Bjerkandera, Ceriporiopsis, Chrysosporium, Coprinus, Coriolus, Cryptococcus, Filibasidium, Fusarium, Humicola, Magnaporthe, Mucor, Myceliophthora, Neocallimastix, Neurospora, Paecilomyces, Penicillium, Phanerochaete, Phlebia, Piromyces, Pleurotus, Schizophyllum, Talaromyces, Thermoascus, Thielavia, Tolypocladium, Trametes,* or *Trichoderma* cell.

In a most preferred aspect, the filamentous fungal host cell is an *Aspergillus awamori, Aspergillus fumigatus, Aspergillus foetidus, Aspergillus japonicus, Aspergillus nidulans, Aspergillus niger* or *Aspergillus oryzae* cell. In another most preferred aspect, the filamentous fungal host cell is a *Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium sporotrichioides, Fusarium sulphureum, Fusarium torulosum, Fusarium trichothecioides,* or *Fusarium venenatum* cell. In another most preferred aspect, the filamentous fungal host cell is a *Bjerkandera adusta, Ceriporiopsis aneirina, Ceriporiopsis aneirina, Ceriporiopsis caregiea, Ceriporiopsis gilvescens, Ceriporiopsis pannocinta, Ceriporiopsis rivulosa, Ceriporiopsis subrufa, Ceriporiopsis subvermispora, Chrysosporium keratinophilum, Chrysosporium lucknowense, Chrysosporium tropicum, Chrysosporium merdarium, Chrysosporium inops, Chrysosporium pannicola, Chrysosporium queenslandicum, Chrysosporium zonatum, Coprinus cinereus, Coriolus hirsutus, Humicola insolens, Humicola lanuginosa, Mucor miehei, Myceliophthora thermophila, Neurospora crassa, Penicillium purpurogenum, Phanerochaete chrysosporium, Phlebia radiata, Pleurotus eryngii, Thielavia terrestris, Trametes villosa, Trametes versicolor, Trichoderma harzianum, Trichoderma koningii, Trichoderma longibrachiatum, Trichoderma reesei,* or *Trichoderma viride* cell.

Fungal cells may be transformed by a process involving protoplast formation, transformation of the protoplasts, and regeneration of the cell wall in a manner known per se. Suitable procedures for transformation of *Aspergillus* and *Trichoderma* host cells are described in EP 238 023 and Yelton et al., 1984, *Proceedings of the National Academy of Sciences USA* 81: 1470-1474. Suitable methods for transforming *Fusarium* species are described by Malardier et al., 1989, *Gene* 78: 147-156, and WO 96/00787. Yeast may be transformed using the procedures described by Becker and Guarente, In Abelson, J. N. and Simon, M. I., editors, *Guide to Yeast Genetics and Molecular Biology, Methods in Enzymology,* Volume 194, pp 182-187, Academic Press, Inc., New York; Ito et al., 1983, *Journal of Bacteriology* 153: 163; and Hinnen et al., 1978, *Proceedings of the National Academy of Sciences USA* 75: 1920.

Methods of Production

The present invention also relates to methods of producing a polypeptide of the present invention, comprising: (a) cultivating a cell, which in its wild-type form produces the polypeptide, under conditions conducive for production of the polypeptide; and (b) recovering the polypeptide. In a preferred aspect, the cell is of the genus *Trichophaea*. In a more preferred aspect, the cell is *Trichophaea saccata*. In a most preferred aspect, the cell is *Trichophaea saccata* CBS804.70.

The present invention also relates to methods of producing a polypeptide of the present invention, comprising: (a) cultivating a recombinant host cell, as described herein, under conditions conducive for production of the polypeptide; and (b) recovering the polypeptide.

The present invention also relates to methods of producing a polypeptide of the present invention, comprising: (a) cultivating a recombinant host cell under conditions conducive for production of the polypeptide, wherein the host cell comprises a mutant nucleotide sequence having at least one mutation in the mature polypeptide coding sequence of SEQ ID NO: 1, wherein the mutant nucleotide sequence encodes a polypeptide that comprises or consists of the mature polypeptide of SEQ ID NO: 2, and (b) recovering the polypeptide.

In the production methods of the present invention, the cells are cultivated in a nutrient medium suitable for production of the polypeptide using methods well known in the art. For example, the cell may be cultivated by shake flask cultivation, and small-scale or large-scale fermentation (including continuous, batch, fed-batch, or solid state fermentations) in laboratory or industrial fermentors performed in a suitable medium and under conditions allowing the polypeptide to be expressed and/or isolated. The cultivation takes place in a suitable nutrient medium comprising carbon and nitrogen sources and inorganic salts, using procedures known in the art. Suitable media are available from commercial suppliers or may be prepared according to published compositions (e.g., in catalogues of the American Type Culture Collection). If the polypeptide is secreted into the nutrient medium, the polypeptide can be recovered directly from the medium. If the polypeptide is not secreted into the medium, it can be recovered from cell lysates.

The polypeptides may be detected using methods known in the art that are specific for the polypeptides. These detection methods may include use of specific antibodies, formation of an enzyme product, or disappearance of an enzyme substrate. For example, an enzyme assay may be used to determine the activity of the polypeptide as described herein.

The resulting polypeptide may be recovered using methods known in the art. For example, the polypeptide may be recovered from the nutrient medium by conventional procedures including, but not limited to, centrifugation, filtration, extraction, spray-drying, evaporation, or precipitation.

The polypeptides of the present invention may be purified by a variety of procedures known in the art including, but not limited to, chromatography (e.g., ion exchange, affinity, hydrophobic, chromatofocusing, and size exclusion), electrophoretic procedures (e.g., preparative isoelectric focusing), differential solubility (e.g., ammonium sulfate precipitation), SDS-PAGE, or extraction (see, e.g., *Protein Purification*, J.-C. Janson and Lars Ryden, editors, VCH Publishers, New York, 1989) to obtain substantially pure polypeptides.

Removal or Reduction of Tyrosinase Activity

The present invention also relates to methods of producing a mutant of a parent cell, which comprises disrupting or deleting a polynucleotide sequence, or a portion thereof, encoding a polypeptide of the present invention, which results in the mutant cell producing less of the polypeptide than the parent cell when cultivated under the same conditions.

The mutant cell may be constructed by reducing or eliminating expression of a nucleotide sequence encoding a polypeptide of the present invention using methods well known in the art, for example, insertions, disruptions, replacements, or deletions. In a preferred aspect, the nucleotide sequence is inactivated. The nucleotide sequence to be modified or inactivated may be, for example, the coding region or a part thereof essential for activity, or a regulatory element required for the expression of the coding region. An example of such a regulatory or control sequence may be a promoter sequence or a functional part thereof, i.e., a part that is sufficient for affecting expression of the nucleotide sequence. Other control sequences for possible modification include, but are not limited to, a leader, polyadenylation sequence, propeptide sequence, signal peptide sequence, transcription terminator, and transcriptional activator.

Modification or inactivation of the nucleotide sequence may be performed by subjecting the parent cell to mutagenesis and selecting for mutant cells in which expression of the nucleotide sequence has been reduced or eliminated. The mutagenesis, which may be specific or random, may be performed, for example, by use of a suitable physical or chemical mutagenizing agent, by use of a suitable oligonucleotide, or by subjecting the DNA sequence to PCR generated mutagenesis. Furthermore, the mutagenesis may be performed by use of any combination of these mutagenizing agents.

Examples of a physical or chemical mutagenizing agent suitable for the present purpose include ultraviolet (UV) irradiation, hydroxylamine, N-methyl-N'-nitro-N-nitrosoguanidine (MNNG), O-methyl hydroxylamine, nitrous acid, ethyl methane sulphonate (EMS), sodium bisulphite, formic acid, and nucleotide analogues.

When such agents are used, the mutagenesis is typically performed by incubating the parent cell to be mutagenized in the presence of the mutagenizing agent of choice under suitable conditions, and screening and/or selecting for mutant cells exhibiting reduced or no expression of the gene.

Modification or inactivation of the nucleotide sequence may be accomplished by introduction, substitution, or removal of one or more (several) nucleotides in the gene or a regulatory element required for the transcription or translation thereof. For example, nucleotides may be inserted or removed so as to result in the introduction of a stop codon, the removal of the start codon, or a change in the open reading frame. Such modification or inactivation may be accomplished by site-directed mutagenesis or PCR generated mutagenesis in accordance with methods known in the art. Although, in principle, the modification may be performed in vivo, i.e., directly on the cell expressing the nucleotide sequence to be modified, it is preferred that the modification be performed in vitro as exemplified below.

An example of a convenient way to eliminate or reduce expression of a nucleotide sequence by a cell is based on techniques of gene replacement, gene deletion, or gene disruption. For example, in the gene disruption method, a nucleic acid sequence corresponding to the endogenous nucleotide sequence is mutagenized in vitro to produce a defective nucleic acid sequence that is then transformed into the parent cell to produce a defective gene. By homologous recombination, the defective nucleic acid sequence replaces the endogenous nucleotide sequence. It may be desirable that the defective nucleotide sequence also encodes a marker that may be used for selection of transformants in which the nucleotide sequence has been modified or destroyed. In a particularly preferred aspect, the nucleotide sequence is disrupted with a selectable marker such as those described herein.

Alternatively, modification or inactivation of the nucleotide sequence may be performed by established anti-sense or RNAi techniques using a sequence complementary to the nucleotide sequence. More specifically, expression of the nucleotide sequence by a cell may be reduced or eliminated by introducing a sequence complementary to the nucleotide sequence of the gene that may be transcribed in the cell and is capable of hybridizing to the mRNA produced in the cell. Under conditions allowing the complementary anti-sense nucleotide sequence to hybridize to the mRNA, the amount of protein translated is thus reduced or eliminated.

The present invention further relates to a mutant cell of a parent cell that comprises a disruption or deletion of a nucleotide sequence encoding the polypeptide or a control sequence thereof, which results in the mutant cell producing less of the polypeptide or no polypeptide compared to the parent cell.

The polypeptide-deficient mutant cells so created are particularly useful as host cells for the expression of native and/or heterologous polypeptides. Therefore, the present invention further relates to methods of producing a native or heterologous polypeptide comprising: (a) cultivating the mutant cell under conditions conducive for production of the polypeptide; and (b) recovering the polypeptide. The term "heterologous polypeptides" is defined herein as polypeptides that are not native to the host cell, a native protein in which modifications have been made to alter the native sequence, or a native protein whose expression is quantitatively altered as a result of a manipulation of the host cell by recombinant DNA techniques.

In a further aspect, the present invention relates to a method of producing a protein product essentially free of tyrosinase activity by fermentation of a cell that produces both a polypeptide of the present invention as well as the protein product of interest by adding an effective amount of an agent capable of inhibiting tyrosinase activity to the fermentation broth before, during, or after the fermentation has been completed, recovering the product of interest from the fermentation broth, and optionally subjecting the recovered product to further purification.

In a further aspect, the present invention relates to a method of producing a protein product essentially free of tyrosinase activity by cultivating the cell under conditions permitting the expression of the product, subjecting the resultant culture broth to a combined pH and temperature treatment so as to reduce the tyrosinase activity substantially, and recovering the product from the culture broth. Alternatively, the combined pH and temperature treatment may be performed on an enzyme preparation recovered from the culture broth. The combined pH and temperature treatment may optionally be used in combination with a treatment with a tyrosinase inhibitor.

In accordance with this aspect of the invention, it is possible to remove at least 60%, preferably at least 75%, more preferably at least 85%, still more preferably at least 95%, and most preferably at least 99% of the tyrosinase activity. Complete removal of tyrosinase activity may be obtained by use of this method.

The combined pH and temperature treatment is preferably carried out at a pH in the range of 2-4 or 9-11 and a temperature in the range of at least 60-70° C. for a sufficient period of time to attain the desired effect, where typically, 30 to 60 minutes is sufficient.

The methods used for cultivation and purification of the product of interest may be performed by methods known in the art.

The methods of the present invention for producing an essentially tyrosinase-free product is of particular interest in the production of eukaryotic polypeptides, in particular fungal proteins such as enzymes. The enzyme may be selected from, e.g., an amylolytic enzyme, lipolytic enzyme, proteolytic enzyme, cellulytic enzyme, oxidoreductase, or plant cell-wall degrading enzyme. Examples of such enzymes include an aminopeptidase, amylase, amyloglucosidase, carbohydrase, carboxypeptidase, catalase, cellobiohydrolase, cellulase, chitinase, cutinase, cyclodextrin glycosyltransferase, deoxyribonuclease, endoglucanase, esterase, galactosidase, beta-galactosidase, glucoamylase, glucose oxidase, glucosidase, haloperoxidase, hemicellulase, invertase, isomerase, laccase, ligase, lipase, lyase, mannosidase, oxidase, pectinolytic enzyme, peroxidase, phytase, phenoloxidase, polyphenoloxidase, proteolytic enzyme, ribonuclease, transferase, transglutaminase, or xylanase. The tyrosinase-deficient cells may also be used to express heterologous proteins of pharmaceutical interest such as hormones, growth factors, receptors, and the like.

It will be understood that the term "eukaryotic polypeptides" includes not only native polypeptides, but also those polypeptides, e.g., enzymes, which have been modified by amino acid substitutions, deletions or additions, or other such modifications to enhance activity, thermostability, pH tolerance and the like.

In a further aspect, the present invention relates to a protein product essentially free from tyrosinase activity that is produced by a method of the present invention.

Compositions

The present invention also relates to compositions comprising a polypeptide of the present invention. Preferably, the compositions are enriched in such a polypeptide. The term "enriched" indicates that the tyrosinase activity of the composition has been increased, e.g., with an enrichment factor of at least 1.1.

The composition may comprise a polypeptide of the present invention as the major enzymatic component, e.g., a mono-component composition. Alternatively, the composition may comprise multiple enzymatic activities, such as an aminopeptidase, amylase, carbohydrase, carboxypeptidase, catalase, cellulase, chitinase, cutinase, cyclodextrin glycosyltransferase, deoxyribonuclease, esterase, alpha-galactosidase, beta-galactosidase, glucoamylase, alpha-glucosidase, beta-glucosidase, haloperoxidase, invertase, laccase, lipase, mannosidase, oxidase, pectinolytic enzyme, peptidoglutaminase, peroxidase, phytase, polyphenoloxidase, proteolytic enzyme, ribonuclease, transglutaminase, or xylanase. The additional enzyme(s) may be produced, for example, by a microorganism belonging to the genus *Aspergillus*, preferably *Aspergillus aculeatus*, *Aspergillus awamori*, *Aspergillus fumigatus*, *Aspergillus foetidus*, *Aspergillus japonicus*, *Aspergillus nidulans*, *Aspergillus niger*, or *Aspergillus oryzae*; *Fusarium*, preferably *Fusarium bactridioides*, *Fusarium cerealis*, *Fusarium crookwellense*, *Fusarium culmorum*, *Fusarium graminearum*, *Fusarium graminum*, *Fusarium heterosporum*, *Fusarium negundi*, *Fusarium oxysporum*, *Fusarium reticulatum*, *Fusarium roseum*, *Fusarium sambucinum*, *Fusarium sarcochroum*, *Fusarium sulphureum*, *Fusarium toruloseum*, *Fusarium trichothecioides*, or *Fusarium venenatum*; *Humicola*, preferably *Humicola insolens* or *Humicola lanuginosa*; or *Trichoderma*, preferably *Trichoderma harzianum*, *Trichoderma koningii*, *Trichoderma longibrachiatum*, *Trichoderma reesei*, or *Trichoderma viride*.

The polypeptide compositions may be prepared in accordance with methods known in the art and may be in the form of a liquid or a dry composition. For instance, the polypeptide composition may be in the form of a granulate or a microgranulate. The polypeptide to be included in the composition may be stabilized in accordance with methods known in the art.

Examples are given below of preferred uses of the polypeptide compositions of the invention. The dosage of the polypeptide composition of the invention and other conditions under which the composition is used may be determined on the basis of methods known in the art.

Uses

The present invention is also directed to methods for using the polypeptides having tyrosinase activity, or compositions thereof.

The polypeptides of the present invention are useful in formation of quinones to any kind of matrices comprising phenolic groups reactive therewith with subsequent formation of cross-linking as for example in protein matrices.

The polypeptides of the present invention may be used for treating any protein containing material, and especially proteins that have a relatively high overall-content or relatively high content of accessible tyrosine residues. Also tyrosine-containing peptides can be modified. The polypeptides of the present invention may be applied in different types of industrial applications, such as in the pharmaceutical, cosmetic, pulp and paper, detergent, and textile industry, and in the feed and food industry. The present invention therefore in one aspect relates to a method of modifying a protein-containing material, wherein said material is contacted with a polypeptide of the invention.

The polypeptides of the present invention are especially suitable for treating protein-containing material, wherein the treatment comprises cross-linking of tyrosine-containing proteins.

The polypeptides of the present invention are especially suitable for treating protein-containing food, particularly meat, dairy, vegetable and cereal materials. By cross-linking food proteins with a polypeptide of the present invention, the texture and rheological properties of the food product can be improved. The present invention therefore in one aspect relates to a method of modifying a protein-containing food material, wherein said material is contacted with a polypeptide of the invention. In a preferred aspect, the present invention relates to a method of modifying a material comprising meat protein, wherein said material is contacted with a polypeptide of the invention. The meat protein may be any kind of meat, including fish meat. In another preferred aspect, the present invention relates to a method of modifying a material comprising dairy protein, wherein said material is contacted with a polypeptide of the invention. In another preferred aspect, the present invention relates to a method of modifying a material comprising vegetable protein, wherein said material is contacted with a polypeptide of the invention. In another preferred aspect, the present invention relates to a method of modifying a cereal-based protein-containing material, wherein said material is contacted with a polypeptide of the invention.

Treatment of e.g. fish, poultry or other meat products with the polypeptides of the present invention may be useful for obtaining a product with good texture using decreased quantities of other structure forming agents. The polypeptides may also be used for gelling, whereby the use of gelatin can be avoided. The polypeptides may further be used for preventing syneresis i.e. separation of the water phase, which is a problem in a number of milk products, especially if the fat content is low. For example in preparing yoghurt, and especially low calorie yoghurt, the solid and the liquid phase tend to separate during storage. This is disapproved by the consumer, and can be prevented by treating the raw materials in yoghurt with a polypeptide according to the present invention. In a preferred aspect, the present invention relates to a method of producing a yoghurt product comprising treatment of a dairy protein containing material with a polypeptide of the invention. In another preferred aspect, the present invention relates to a method of producing an acidified milk drink comprising treatment of a dairy protein containing material with a polypeptide of the invention.

The polypeptides may also be applied in bakery processes e.g. for hardening the dough, which is especially desired in making frozen dough products. In a preferred aspect, the present invention therefore relates to a method of producing a bakery product comprising treatment of a cereal-based protein containing material with a polypeptide of the invention.

The polypeptides of the present invention are especially suitable for producing bio-adhesives, such as marine bio-adhesives, medical bio-adhesives, tissue bio-adhesives or food adhesives. In a preferred aspect, the present invention relates to a method of producing a bio-adhesive comprising treatment of a protein containing material with a polypeptide of the invention. In a more preferred aspect, the present invention relates to a method of producing a medical bio-adhesive comprising treatment of a protein containing material with a polypeptide of the invention.

The polypeptides may further be used for producing L-Dopa, which is useful in the treatment of Parkinson's disease, and in the production of melanins, which are ingredients for the cosmetic industry. In addition, the polypeptides may be used for cross-linking proteinaceous fibres or fibre-derived polymers, such as silk, wool, cashmere, alpaca, or human hair.

The present invention is further described by the following examples that should not be construed as limiting the scope of the invention.

EXAMPLES

Chemicals used as buffers and substrates were commercial products of at least reagent grade.

Strains

*Trichophaea saccata* strain CBS 804.70 was used as the source of a gene encoding a tyrosinase. *Trichophaea saccata* CBS 804.70 is available from the Centraalbureau voor Schimmelcultures.

*Aspergillus oryzae* Ja1250 strain (WO 99/61651) was used for expression of the *Trichophaea saccata* CBS 804.70 tyrosinase.

Media

MEX-1 medium was composed per liter of 20 g of soy bean meal, 15 g of wheat bran, 10 g of microcrystalline cellulose (AVICEL®; FMC, Philadelphia, Pa., USA), 5 g of maltodextrin, 3 g of Bactopeptone, 0.2 g of pluronic, and 1 g of olive oil.

PDA plates were composed per liter of 39 grams of potato dextrose agar.

LB medium was composed per liter of 10 g of tryptone, 5 g of yeast extract, and 5 g of sodium chloride.

LB plates were composed of LB medium and 15 g of Bacto agar per liter.

SOC medium was composed of 2% tryptone, 0.5% yeast extract, 10 mM NaCl, 2.5 mM KCl, 10 mM $MgCl_2$, and 10 mM $MgSO_4$, sterilized by autoclaving and then filter-sterilized glucose was added to 20 mM.

MDU2BP medium was composed per liter of 45 g of maltose, 1 g of $MgSO_4.7H_2O$, 1 g of NaCl, 2 g of $K_2HSO_4$, 12 g of $KH_2PO_4$, 2 g of urea, and 500 µl of AMG trace metals solution. The pH was adjusted to 5.0 and then filter sterilized using a 0.22 µm filtering unit.

AMG trace metals solution was composed per liter of 14.3 g of $ZnSO_4.7H_2O$, 2.5 g of $CuSO_4.5H_2O$, 0.5 g of $NiCl_2.6H_2O$, 13.8 g of $FeSO_4.7H_2O$, 8.5 citric acid.

2× YT plates were composed per liter of 16 g of tryptone, 10 g of yeast extract, 5 g of NaCl, and 15 g of bacto agar.

Example 1

Preparation of *Trichophaea saccata* Strain CBS 804.70 Mycelia for cDNA Library Production

*Trichophaea saccata* CBS 804.70 was inoculated onto a PDA plate and incubated for 7 days at 28° C. Several mycelia-PDA agar plugs were inoculated into 750 ml shake flasks containing 100 ml of MEX-1 medium. The flasks were agitated at 150 rpm for 9 days at 37° C. The fungal mycelia were harvested by filtration through MIRACLOTH® (Calbiochem, San Diego, Calif., USA) before being frozen in liquid nitrogen. The mycelia were then pulverized into a powder by milling the frozen mycelia together with an equal volume of dry ice in a Krups KM 75 coffee grinder precooled with liquid nitrogen. The powder was transferred into a liquid nitrogen prechilled mortor and pestle and ground to a fine powder with a small amount of baked quartz sand. The powdered mycelial material was kept at −80° C. until use.

Example 2

*Trichophaea saccata* Strain CBS 804.70 RNA Isolation

Total RNA was prepared from the frozen, powdered mycelium of *Trichophaea saccata* CBS 804.70 by extraction with guanidium thiocyanate followed by ultracentrifugation through a 5.7 M CsCI cushion according to Chirgwin et al., 1979, *Biochemistry* 18: 5294-5299. The polyA enriched RNA was isolated by oligo (dT)-cellulose affinity chromatography according to Aviv et al., 1972, *Proc. Natl. Acad. Sci. USA* 69: 1408-1412.

Example 3

Construction of a *Trichophaea saccata* Strain CBS 804.70 cDNA Library

Double stranded cDNA was synthesized according to the general methods of Gubler and Hoffman, 1983, *Gene* 25: 263-269; Sambrook, J., Fritsch, E. F., and Maniantis, T. *Molecular cloning: A Laboratory Manual*, $2^{nd}$ ed., 1989, Cold Spring Harbor Laboratory, Cold Spring Harbor, N.Y.; and Kofod et al. (1994) using a polyA-Not I primer (Promega Corp., Madison, Wis., USA). After synthesis, the cDNA was treated with mung bean nuclease, blunt ended with T4 DNA polymerase, and ligated to a 50-fold molar excess of Eco RI adaptors (Invitrogen Corp., Carlsbad, Calif., USA). The cDNA was cleaved with Not I (New England Biolabs, USA) according to the manufacturer's instructions and the cDNA was size fractionated by 0.8% agarose gel electrophoresis using in 44 mM Tris base, 44 mM boric acid, 0.5 mM EDTA (TBE) buffer. The fraction of cDNA of 700 bp and larger was excised from the gel and purified using a GFX® PCR DNA and Gel Band Purification Kit according to the manufacturer's instructions (Amersham Biosciences, United Kingdom).

The prepared cDNA was then directionally cloned by ligation into Eco RI-Not I cleaved pMHas5 (WO 03/044049) using a Rapid Ligation Kit (Roche Diagnostics GmbH, Penzberg, Germany) according to the manufacturer's instructions. The ligation mixture was electroporated into *E. coli* DH10B cells (Carlsbad, Calif., USA) using a GENE PULSER® and Pulse Controller (Bio-Rad, Hercules, Calif., USA) at 50 uF, 25 mAmp, 1.8 kV with a 2 mm gap cuvette according to the manufacturer's procedure.

The electroporated cells were plated onto LB plates supplemented with 50 µg of kanamycin per m. A cDNA plasmid pool was prepared from 30,000 total transformants of the original cDNA-pMHas5 vector ligation. Plasmid DNA was prepared directly from the pool of colonies using a QIAPREP® Spin Midi/Maxiprep Kit (QIAGEN GmbH Corporation, Hilden, Germany). The cDNA library was designated SBL521-2.

Example 4

Construction of a SigA4 Transposon Containing the β-Lactamase Reporter Gene

A transposon containing plasmid designated pSigA4 was constructed from the pSigA2 transposon containing plasmid described in patent WO 01/77315 in order to create an improved version of the signal trapping transposon of pSigA2 with decreased selection background. The pSigA2 transposon contains a signal less betalactamase construct encoded on the transposon itself. PCR was used to create a deletion of the intact beta lactamase gene found on the plasmid backbone using a proofreading Pfu Turbo polymerase ProofStart (QIAGEN GmbH Corporation, Hilden, Germany) and the following 5' phosphorylated primers (TAG Copenhagen, Denmark):

```
SigA2NotU-P:
                                          (SEQ ID NO: 3)
5'-TCGCGATCCGTTTTCGCATTTATCGTGAAACGCT-3'

SigA2NotD-P:
                                          (SEQ ID NO: 4)
5'-CCGCAAACGCTGGTGAAAGTAAAAGATGCTGAA-3'
```

The amplification reaction was composed of 1 µl of pSigA2 (10 ng/µl), 5 µl of 10× ProofStart Buffer (QIAGEN GmbH Corporation, Hilden, Germany), 2.5 µl of dNTP mix (20 mM), 0.5 µl of SigA2NotU-P (10 mM), 0.5 µl of SigA2NotD-P (10 mM), 10 µl of Q solution (QIAGEN GmbH Corporation, Hilden, Germany), and 31.25 µl of deionized water. A DNA ENGINE™ Thermal Cycler (MJ Research Inc., Waltham, Mass., USA) was used for amplification programmed for one cycle at 95° C. for 5 minutes; and 20 cycles each at 94° C. for 30 seconds, 62° C. for 30 seconds, and 72° C. for 4 minutes.

A 3.9 kb PCR reaction product was isolated on a 0.8% agarose gel using 40 mM Tris base-20 mM sodium acetate-1 mM disodium EDTA (TAE) buffer and 0.1 µg of ethidium bromide per ml. The DNA band was visualized with the aid of an Eagle Eye Imaging System (Stratagene, La Jolla, Calif., USA) at 360 nm. The 3.9 kb DNA band was excised from the gel and purified by using a GFX® PCR DNA and Gel Band Purification Kit (GE Healthcare, United Kingdom) according to the manufacturer's instructions.

The 3.9 kb fragment was self-ligated at 16° C. overnight with 10 units of T4 DNA ligase (New England Biolabs, Inc., Beverly, Mass., USA), 9 µl of the 3.9 kb PCR fragment, and 1 µl of 10× ligation buffer (New England Biolabs, Inc., Beverly, Mass., USA). The ligation was heat inactivated for 10 minutes at 65° C. and then digested with Dpn I at 37° C. for 2 hours. After incubation, the digestion was purified using a GFX® PCR DNA and Gel Band Purification Kit.

The purified material was then transformed into *E. coli* Top10 competent cells (Invitrogen Corp., Carlsbad, Calif., USA) according to the manufacturer's instructions. The transformation mixture was plated onto LB plates supplemented with 25 µg of chloramphenicol per ml. Plasmid minipreps were prepared from several transformants and digested with Bgl II. One plasmid with the correct construction was chosen. The plasmid was designated pSigA4. Plasmid pSigA4 contains the Bgl II flanked transposon SigA2 (SEQ ID NO: 5) identical to that disclosed in WO 01/77315.

A 60 µl sample of plasmid pSigA4 DNA (0.3 µg/µl) was digested with Bgl II and separated on a 0.8% agarose gel using TE (10 mM Tris-0.1 mM EDTA pH 7.4) buffer. A SigA2 transposon DNA band of 2 kb was eluted with 200 µl of EB buffer (QIAGEN GmbH Corporation, Hilden, Germany) and purified using a GFX® PCR DNA and Gel Band Purification Kit according to the manufacturer's instructions and eluted in 200 µl of EB buffer. SigA2 was used for transposon assisted signal trapping.

Example 5

Transposon Assisted Signal Trapping of *Trichophaea saccata* CBS 247.96

A complete description of transposon assisted signal trapping can be found in WO 01/77315. A cDNA plasmid pool was prepared from 30,000 total transformants of the original cDNA-pMHas5 vector ligation. Plasmid DNA was prepared directly from a pool of colonies recovered from solid LB selective medium using a QIAPREP® Spin Midi/Maxiprep Kit. The plasmid pool was treated with transposon SigA2 and MuA transposase (Finnzymes O Y, Espoo, Finland) according to the manufacturer's instructions.

For in vitro transposon tagging of the *Trichophaea saccata* CBS 247.96 cDNA library, 4 or 8 µl of SigA2 transposon containing approximately 2.6 µg of DNA were mixed with 1 µl of the plasmid DNA pool of the *Trichophaea saccata* CBS 804.70 cDNA library containing 2 µg of DNA, 2 µl of MuA transposase (0.22 µg/µl), and 5 µl of 5× buffer (Finnzymes O Y, Espoo, Finland) in a total volume of 50 µl and incubated at 30° C. for 3.5 hours followed by heat inactivation at 75° C. for 10 minutes. The DNA was precipitated by addition of 5 µl of 3 M sodium acetate pH 5 and 110 µl of 96% ethanol and centrifuged for 30 minutes at 10,000×g. The pellet was washed in 70% ethanol, air dried at room temperature, and resuspended in 10 µl of 10 mM Tris, pH 8, 1 mM EDTA (TE) buffer.

A 1.5 µl volume of the transposon tagged plasmid pool was electroporated into 20 µl of *E. coli* DH10B ultracompetent cells (Gibco-BRL, Gaithersburg Md., USA) according to the manufacturer's instructions using a GENE PULSER® and Pulse Controller (Bio-Rad, Hercules, Calif., USA) at 50 uF, 25 mAmp, 1.8 kV with a 2 mm gap cuvette according to the manufacturer's procedure.

The electroporated cells were incubated in SOC medium with shaking at 250 rpm for 2 hours at 28° C. before being plated on the following selective media: LB medium supplemented with 50 μg of kanamycin per ml; LB medium supplemented with 50 μg of kanamycin per ml and 15 μg of chloramphencol per ml; and/or LB medium supplemented with 50 μg of kanamycin per ml, 15 μg of chloramphencol per ml, and 12.5 μg of ampicillin per ml.

From dilution plating of the electroporation onto LB medium supplemented with kanamycin and chloramphencol medium, it was determined that approximately 72,000 colonies were present containing a cDNA library plasmid with a SigA2 transposition per electroporation and that approximately 69 colonies were recovered under triple selection (LB, kanamycin, chorlamphenicol, ampicillin). Further electroporation and plating experiments were performed until 445 total colonies were recovered under triple selection. The colonies were miniprepped using a QIAPREP® 96 Turbo Miniprep Kit (QIAGEN GmbH Corporation, Hilden, Germany). Plasmids were sequenced with the transposon forward and reverse primers (primers A and B), shown below, according to the procedure disclosed in WO 01/77315 (page 28)

```
Primer A:
5'-AGCGTTTGCGGCCGCGATCC-3'         (SEQ ID NO: 6)

Primer B:
5'-TTATTCGGTCGAAAAGGATC C-3'       (SEQ ID NO: 7)
```

Example 6

Sequence Assembly and Annotation

DNA sequences were obtained for the reactions on an ABI PRISM Automated DNA Sequencer Model 3700 (Applied Biosystems, Foster City, Calif., USA). Primer A and primer B sequence reads for each plasmid were trimmed to remove vector and transposon sequence. This resulted in 225 assembled sequences which were grouped into 148 contigs by using the program PhredPhrap (Ewing et al., 1998, *Genome Research* 8: 175-185; Ewing and Green, 1998, *Genome Research* 8: 186-194). All 148 contigs were subsequently compared to sequences available in standard public DNA and protein sequences databases (TrEMBL, SWALL, PDB, EnsemblPep, GeneSeqP) by using the program BLASTX 2.0a19MP-WashU [14 Jul. 1998] [Build linux-x86 18:51:44 30 Jul. 1998] (Gish et al., 1993, *Nat. Genet.* 3: 266-72). The tyrosinase candidate was identified directly by analysis of the BlastX results.

The open reading frame for the DNA contig was easily extracted from the assembly of 15 independent transposition events positioned essentially randomly along the coding region. The nucleotide sequence (SEQ ID NO: 1) and deduced amino acid sequence (SEQ ID NO: 2) are shown in the sequence listing. The cDNA fragment encodes a polypeptide of 685 amino acids. The % G+C content of the gene is 58.1%. Using the SignalP software program (Nielsen et al., 1997, *Protein Engineering* 10: 1-6), a signal peptide of 24 residues was predicted. The predicted mature protein contains 661 amino acids with a predicted molecular mass of 73 kDa.

A comparative alignment of tyrosinase sequences was determined using the Clustal W method (Higgins, 1989, supra) using the AlignX module of the vector NTI Advance 10.3 software (Invitrogen Corp., Carlsbad, Calif., USA) with a blosum62mt2 scoring matrix and the following multiple alignment parameters: K-tuple size 1; best diagonals 5; window size 5; gap penalty 5; gap opening penalty 10; gap extension penalty 0.1. The alignment showed that the deduced amino acid sequence of the mature *Trichophaea saccata* tyrosinase enzyme shares 31% identity to the deduced amino acid sequence of the mature sequence of the closest relative in the public domain (GeneSeqP:AEJ90975). AEJ90975 is tyrosinase TYR1 from *Trichoderma reesei* listed in patent WO2006084953-A1.

TABLE 1

|  | A6SQE9 | A7F6Y4 | AEJ90975 | A7EHD3 | SeqID2 |
|---|---|---|---|---|---|
| A6SQE9_BOTFB | — | 81 | 44 | 32 | 30 |
| A7F6Y4_SCLS1 | — | — | 44 | 33 | 29 |
| AEJ90975 | — | — | — | 34 | 31 |
| A7EHD3_SCLS1 | — | — | — | — | 26 |
| Seq ID 2 | — | — | — | — | — |

Amino acid sequence identity of the sequence of the invention with the three most closely related sequences identified in the public databases GeneSeqP and UniProt. Identity values were generated as described in the text.

Example 7

Expression of Tyrosinase from *Trichophaea saccata* CBS 804.70

The sequence identified in the previous section (Seq ID no. 1) was used to design two PCR primers that were used for producing a DNA expression cassette suitable for cloning into the *Aspergillus oryzae* expression plasmid pXYG1051 (WO 2005/080559).

The following primers were used (Restriction sites introduced for cloning purposes are underlined):

```
NP1057RI:
                                    (SEQ ID NO: 8)
5'-GCGGAATTCACCATGAAGTTTTCAGCCTTTGTGGC-3'

NP1057NotI:
                                    (SEQ ID NO: 9)
5'-ATATGCGGCCGCAGGAGTGGAGGTAGGGGTGTAGACCG-3'
```

1 microliter of *Trichophaea saccata* plasmid cDNA library (approximately 10 nanograms of DNA) was used as template in a PCR reaction with the two primers NP1057RI and NP1057NotI.

5 pmol of each primer was used in a 50 microliter reaction volume. The Qiagen ProofStart high fidelity DNA polymerase and buffer were used according to the manufacturer's instructions (Qiagen, USA). Briefly, the reaction was placed in a thermal cycler (MJ Research, Dyad, USA) and cycled under the following reaction conditions: An initial denaturation of 5 minutes at 95 degrees Celsius, 25 cycles of the following: 94 degrees for 30 seconds, 55 degrees for 30 seconds, 72 degrees for 2 minutes. A final extension temperature of 72 degrees for 10 minutes was then used. Aliquots of the PCR reaction were separated on a 1% agarose gel. One band was seen: The size of this band appeared with the expected size of 2058 bp.

The fragment was digested with EcoRI and NotI which cut in the overhangs introduced by the PCR primers. A standard ligation into pXYG1051 and transformation into *E. coli* Top10 cells (Invitrogen) resulted in several plasmids being identified. Plasmid DNA was isolated from colonies of the cloning experiment. The colonies were sequenced with the following vector primers:

```
PNA2
                                    (SEQ ID NO: 10)
5'-GTT TCC AAC TCA ATT TAC CTC-3'

TAMG
                                    (SEQ ID NO: 11)
5'-TTG CCC TCA TCC CCA TCC TTT -3'
``` which prime in opposite directions into the plasmid insert. A single plasmid was chosen for transformation into *Aspergillus oryzae*.

The *Aspergillus* transformation plasmid pSBL521-5 containing SEQ ID NO: 1 was transformed into *Aspergillus oryzae* strain JAL355 (disclosed in international patent application WO 01/98484A1). Transformants of pSBL521-5 were re-isolated twice under selective and non-inducing conditions on Cove minimal plates (Cove (1966) Biochem. Biophys. Acta 133:51-56) with 1M sucrose as a carbon source and 10 mM nitrate. To test expression of SEQ ID NO: 1, transformants were grown for 3 days and 4 days at 30 degrees Celsius in tubes with 10 ml YPG (2% peptone, 1% yeast extract, 2% glucose). Supernatants were run on NuPage® 10% Bis-Tris SDS gels (Invitrogen, USA) as recommended by the manufacturer. All *Aspergillus* isolates grew well on YPG media when induced for the expression of the DNA of SEQ ID NO: 1. One single transformant judged to make sufficient quantities of the tyrosinase was named EXP02003 and was chosen for further fermentation.

Two liters of EXP02003 was fermented in YPM media and the culture fluid was separated from the biomass by miracloth filtration. The tyrosinase was purified from the culture fluid and frozen until further use.

Example 8

Characterization of Tyrosinase from *Trichophaea saccata* pH Profile 20 microliter diluted samples of the tyrosinase of Example 7 (diluted in 20 mM sodium phosphate pH 6.5) were added to a micro titre plate (A280 transparent) and 200 microliter 1 mM tyrosine, 100 mM succinic acid, 100 mM HEPES, 100 mM CHES, 1 mM $CuCl_2$ (various pH, 3-9) were added and incubated for 15 min at 25° C. The reaction was stopped with 20 microliter 4M HCl and the absorbance at 280 nm was measured. The results are shown in the table below.

TABLE 2

| pH | relative activity (pH6 = 100%) |
|---|---|
| 3 | 0.7 |
| 4 | 7.4 |
| 5 | 53 |
| 6 | 100 |

TABLE 2-continued

| pH | relative activity (pH6 = 100%) |
|---|---|
| 7 | 93 |
| 8 | 71 |
| 9 | 0 |

Temperature Profile 10 microliter enzyme sample diluted in 50 mM MES pH 6.5, 1 mM $CuCl_2$ was added to PCR tubes at room temp.

90 microliter preheated (in a Peltier Thermal Cycler 30-70° C.) 50 mM MES pH 6.5, 1 mM tyrosin, 1 mM $CuCl_2$ was added and incubation was performed with a temperature gradient from 40-80° C. for 15 min.

The reaction was stopped by adding 10 microliter 200 mM mM sodium-EDTA followed by a fast temperature increase to 95° C. and incubated for 2 minutes. The solution (room temperature) was transferred to a micro titre plate and absorption at A480 was measured. The results are shown in the table below.

TABLE 3

| Temp (° C.) | relative activity (% of activity at 40° C.) |
|---|---|
| 40 | 100 |
| 40.9 | 96 |
| 43.7 | 89 |
| 48.1 | 72 |
| 52.8 | 52 |
| 57.6 | 25 |
| 62.3 | 12 |
| 67.1 | 4 |
| 71.9 | 3 |
| 76.2 | 0 |
| 79 | 0 |
| 80 | 0 |

Example 9

Use of *T. saccata* Tyrosinase in Production of Liquid Yoghurt

Milk Solution A
    Arla express milk obtained from supermarket in Denmark.
Milk Solution B
    Arla express milk obtained from supermarket in Denmark, pretreated at 95° C. for 5 min.
Sugar Solution
    3.3 g sucrose
    10.5 g glucose
    These sugars were added to 46 ml 20 mM lactic acid buffer, pH 4.0 and incubated at 90° C. for 5 min with stirring and then cooled down to 5° C.
Tyrosinase Solution
    Purified tyrosinase of Example 7, 0.5 mg/ml, in 20 mM bis-Tris, 0.1 mM $CuCl_2$, 100 mM NaCl pH 6.5, 50% glycerol.
Enzyme Dilution Buffer
    50 mM sodium phosphate, pH 7, 0.001% tritonX-100
Procedure A
    375 µl milk solution A was transferred to 2 ml eppendorf tube. 30 µl Tyrosinase solution (0.5 mg/ml, 0.1 mg/ml, 0.02 mg/ml or water) was added and incubation was performed for 120 min at 40° C. The solution was incubated at 85° C. for 30 min in a water bath and hereafter incubated at 43° C. (water bath) for 10 min with mixing (1000 rpm) in an Eppendorf Thermomixer.

45 μl 4 U/IYF-3331 (mixed strain culture containing *Streptococcus thermophilus* and *Lactobacillus delbrueckii* subsp. *bulgaricus* from Chr. Hansen A/S, Denmark) solubilised in milk solution was added and incubation was performed for 16 hours at 43° C.

After 16 hr fermentation the samples were incubated at 0-5° C. ice/water bath for 20 min.

900 μl sugar solution (0-5° C., ice bath) was added and homogenised with ultrasound (4×5 sec with 9 sec pause) on ice bath.

The samples were placed at 5° C. for 1 and 7 days and syneresis was measured.

The syneresis height was measured and the relative syneresis of total milk drink height was calculated. The results are shown in Table 4 below.

Procedure B

375 μl milk solution B was transferred to 2 ml eppendorf tube. 30 μl Tyrosinase solution (0.5 mg/ml, 0.1 mg/ml, 0.02 mg/ml or water) was added and incubation was performed for 120 min at 40° C. The solution was incubated at 85° C. for 30 min in a water bath and hereafter incubated at 43° C. (water bath) for 10 min with mixing (1000 rpm) in an Eppendorf Thermomixer.

45 μl 4 U/IYF-3331 (mixed strain culture containing *Streptococcus thermophilus* and *Lactobacillus delbrueckii* subsp. *bulgaricus* from Chr. Hansen A/S, Denmark) solubilised in milk solution was added and incubation was performed for 16 hours at 43° C.

After 16 hr fermentation the samples were incubated at 0-5° C. ice/water bath for 20 min.

900 μl sugar solution (0-5° C., ice bath) was added and homogenised with ultrasound (4×5 sec with 9 sec pause) on ice bath.

The samples were placed at 5° C. for 1 and 7 days and syneresis was measured.

The syneresis height was measured and the relative syneresis of total milk drink height was calculated. The results are shown in Table 5 below.

Procedure C

375 μl milk solution A (5° C.) was transferred to 2 ml eppendorf tube. 30 μl Tyrosinase solution (0.5 mg/ml, 0.1 mg/ml, 0.02 mg/ml or water) was added and incubation was performed for 24 hr at 5° C. The solution was incubated at 85° C. for 30 min in a water bath and hereafter incubated at 43° C. (water bath) for 10 min with mixing (1000 rpm) in an Eppendorf Thermomixer.

45 μl 4 U/IYF-3331 (mixed strain culture containing *Streptococcus thermophilus* and *Lactobacillus delbrueckii* subsp. *bulgaricus* from Chr. Hansen A/S, Denmark) solubilised in milk solution was added and incubation was performed for 16 hours at 43° C.

After 16 hr fermentation the samples were incubated at 0-5° C. ice/water bath for 20 min.

900 μl sugar solution (0-5° C., ice bath) was added and homogenised with ultrasound (4×5 sec with 9 sec pause) on ice bath.

The samples were placed at 5° C. for 7 days and syneresis was measured.

The syneresis height was measured and the relative syneresis of total milk drink height was calculated. The results are shown in Table 6 below.

Syneresis Data

Double determinations are shown in the tables below. MD is the mean deviation.

TABLE 4

| Procedure A, no pretreatment of milk, 2 hr at 40° C. Tyrosinase conc. added, mg/ml | 1 day storage | | 7 day storage | |
|---|---|---|---|---|
| | Relative syneresis % of total height | MD (+/−) | Relative syneresis % of total height | MD (+/−) |
| 0.5 | 5 | 5 | 34 | 10 |
| 0.1 | 5 | 2 | 35 | 6 |
| 0.02 | 12 | 2 | 57 | 3 |
| water | 52 | 7 | 76 | 2 |

TABLE 5

| Procedure B, pretreated milk, 2 hr at 40° C. Tyrosinase conc. added, mg/ml | 1 day storage | | 7 day storage | |
|---|---|---|---|---|
| | Relative syneresis % of total height | MD (+/−) | Relative syneresis % of total height | MD (+/−) |
| 0.5 | 7 | 3 | 26 | 10 |
| 0.1 | 6 | 2 | 38 | 1 |
| 0.02 | 12 | 3 | 58 | 1 |
| water | 62 | 9 | 78 | 2 |

TABLE 6

| Procedure C, no pretreatment of milk, 24 hr incubation at 5° C. Tyrosinase conc. added, mg/ml | 7 day storage | |
|---|---|---|
| | Relative syneresis % of total height | MD (+/−) |
| 0.5 | 21 | 1 |
| 0.1 | 23 | 1 |
| 0.02 | 27 | 1 |
| water | 76 | 2 |

The data (1 day and 7 days storage) show a dose/response effect of the *T. Saccata* tyrosinase using regular skim milk with a final protein conc. of 1 g/l in the acidified milk drink. In procedure B, the milk has been pre-pasteurized (95°, 5 min), whereas no pretreatment has been performed in procedure A. The tyrosinase is able to preserve the high performance w/o pretreatment and is able to make a significant stabilization at 0.4 mg/l acidified milk drink.

Furthermore when this tyrosinase is incubated at low temp (5° C., see procedure C) at 24 hr, a more pronounced effect is seen at low enzymes dose compared to 40° C., 2 hr treatment. This may be due to the higher oxygen tension at lower temperature.

DEPOSIT OF BIOLOGICAL MATERIAL

The following biological material has been deposited under the terms of the Budapest Treaty with the Deutsche Sammlung von Mikroorganismen und Zellkulturen GmbH (DSM), Mascheroder Weg 1 B, D-38124 Braunschweig, Germany, and given the following accession number:

| Deposit | Accession Number | Date of Deposit |
|---|---|---|
| *E. coli* | DSM 21914 | 17 Oct. 2008 |

The strain has been deposited under conditions that assure that access to the culture will be available during the pendency of this patent application to one determined by foreign patent laws to be entitled thereto. The deposit represents a substantially pure culture of the deposited strain. The deposit is available as required by foreign patent laws in countries wherein counterparts of the subject application, or its progeny are filed. However, it should be understood that the availability of a deposit does not constitute a license to practice the subject invention in derogation of patent rights granted by governmental action.

The invention described and claimed herein is not to be limited in scope by the specific aspects herein disclosed, since these aspects are intended as illustrations of several aspects of the invention. Any equivalent aspects are intended to be within the scope of this invention. Indeed, various modifications of the invention in addition to those shown and described herein will become apparent to those skilled in the art from the foregoing description. Such modifications are also intended to fall within the scope of the appended claims. In the case of conflict, the present disclosure including definitions will control.

The invention claimed is:

1. An isolated polypeptide comprising an amino acid sequence which has at least 85% amino acid sequence identity to the amino acid sequence of amino acids 25 to 431 of SEQ ID NO: 2, wherein the isolated polypeptide has tyrosinase activity.

2. The isolated polypeptide of claim 1, comprising an amino acid sequence having at least 90% amino acid sequence identity to the amino acid sequence of SEQ ID NO: 2.

3. The isolated polypeptide of claim 1, comprising an amino acid sequence having at least 95% amino acid sequence identity to the amino acid sequence of SEQ ID NO: 2.

4. The isolated polypeptide of claim 1, comprising or consisting of the amino acid sequence of SEQ ID NO: 2.

5. The isolated polypeptide of claim 1, which is encoded by a polynucleotide comprising or consisting of the nucleotide sequence of SEQ ID NO: 1; or a polynucleotide comprising or consisting of the nucleotide sequence of nucleotides 73 to 1293 of SEQ ID NO: 1.

6. The isolated polypeptide of claim 1, which is encoded by a polynucleotide comprising or consisting of the nucleotide sequence of nucleotides 73 to 1293 of SEQ ID NO: 1.

7. A method of modifying a protein-containing material comprising tyrosine-containing proteins, the method comprising contacting a protein-containing material comprising tyrosine-containing proteins with the isolated polypeptide of claim 1 to cross-link the tyrosine-containing proteins, thereby modifying the protein-containing material.

8. The method of to claim 7, wherein the protein-containing material is a food material.

9. A composition comprising an isolated polypeptide comprising an amino acid sequence which has at least 85% amino acid sequence identity to the amino acid sequence of amino acids 25 to 431 of SEQ ID NO: 2, wherein the isolated polypeptide has tyrosinase activity.

10. The composition of claim 9, wherein the isolated polypeptide comprises an amino acid sequence having at least 90% amino acid sequence identity to the amino acid sequence of SEQ ID NO: 2.

11. The composition of claim 9, wherein the isolated polypeptide comprises an amino acid sequence having at least 95% amino acid sequence identity to the amino acid sequence of SEQ ID NO: 2.

12. The composition of claim 9, wherein the isolated polypeptide comprises or consists of the amino acid sequence of SEQ ID NO: 2.

13. The composition of claim 9, wherein the isolated polypeptide is encoded by a polynucleotide comprising or consisting of the nucleotide sequence of SEQ ID NO: 1; or a polynucleotide comprising or consisting of the nucleotide sequence of nucleotides 73 to 1293 of SEQ ID NO: 1.

14. The composition of claim 9, wherein the isolated polypeptide is encoded by a polynucleotide comprising or consisting of the nucleotide sequence of nucleotides 73 to 1293 of SEQ ID NO: 1.

* * * * *